US012575790B2

(12) United States Patent
Reuveny

(10) Patent No.: US 12,575,790 B2
(45) Date of Patent: *Mar. 17, 2026

(54) SYSTEMS, APPARATUS, AND METHODS FOR DETECTION AND MONITORING OF CHRONIC SLEEP DISORDERS

(71) Applicant: Wesper Inc., New York, NY (US)

(72) Inventor: Amir Reuveny, New York, NY (US)

(73) Assignee: Wesper Inc., New York, NY (US)

( * ) Notice: Subject to any disclaimer, the term of this patent is extended or adjusted under 35 U.S.C. 154(b) by 742 days.

This patent is subject to a terminal disclaimer.

(21) Appl. No.: 17/974,662

(22) Filed: Oct. 27, 2022

(65) Prior Publication Data

US 2023/0043076 A1     Feb. 9, 2023

Related U.S. Application Data

(63) Continuation of application No. 16/705,806, filed on Dec. 6, 2019, now Pat. No. 11,510,622, which is a
(Continued)

(51) Int. Cl.
*A61B 5/00* (2006.01)
*A61B 5/024* (2006.01)
(Continued)

(52) U.S. Cl.
CPC .......... *A61B 5/6833* (2013.01); *A61B 5/0806* (2013.01); *A61B 5/087* (2013.01);
(Continued)

(58) Field of Classification Search
CPC ... A61B 5/02416; A61B 5/0806; A61B 5/087; A61B 5/113; A61B 5/14551; A61B 5/4809; A61B 5/4815; A61B 5/6833
See application file for complete search history.

(56) References Cited

U.S. PATENT DOCUMENTS

| 5,511,553 A | 4/1996 | Segalowitz |
| 6,811,538 B2 | 11/2004 | Westbrook et al. |
| (Continued) | | |

FOREIGN PATENT DOCUMENTS

| CN | 102525475 A | 7/2012 |
| CN | 104812296 A | 7/2015 |
| (Continued) | | |

OTHER PUBLICATIONS

BodyCompass: Monitoring Sleep Posture with Wireless Signals, 2020, retrieved on Jun. 15, 2021 from http://people.csail.mit.edu/scyue/projects/bodycompass/, 2 pages.
(Continued)

*Primary Examiner* — Christopher A Flory
(74) *Attorney, Agent, or Firm* — Cooley LLP

(57) ABSTRACT

An apparatus for monitoring a sleep parameter of a user includes an adhesive pad configured to conform to a surface of the user and a flexible element coupled to the adhesive pad. The flexible element includes a conductive fabric, and exhibits a modified electrical property in response to an applied force. The apparatus also includes a power source electrically coupled to the flexible element, and an electrical circuit electrically coupled to the power source and the flexible conductive element. The electrical circuit is configured to detect, during use, a change in an electrical property of the flexible element.

20 Claims, 35 Drawing Sheets

Related U.S. Application Data continuation of application No. 16/404,825, filed on May 7, 2019, now Pat. No. 10,531,833, which is a continuation of application No. 16/152,649, filed on Oct. 5, 2018, now Pat. No. 10,531,832.

(60) Provisional application No. 62/569,783, filed on Oct. 9, 2017.

(51) Int. Cl.

| | |
|---|---|
| *A61B 5/08* | (2006.01) |
| *A61B 5/087* | (2006.01) |
| *A61B 5/113* | (2006.01) |
| *A61B 5/1455* | (2006.01) |

(52) U.S. Cl.
CPC .......... *A61B 5/113* (2013.01); *A61B 5/14551* (2013.01); *A61B 5/4809* (2013.01); *A61B 5/4815* (2013.01); *A61B 5/4818* (2013.01); *A61B 5/02416* (2013.01); *A61B 2560/0214* (2013.01); *A61B 2560/0247* (2013.01); *A61B 2560/0412* (2013.01); *A61B 2562/0204* (2013.01); *A61B 2562/0219* (2013.01); *A61B 2562/0261* (2013.01); *A61B 2562/164* (2013.01)

(56) References Cited

U.S. PATENT DOCUMENTS

| | | | |
|---|---|---|---|
| 7,155,981 | B2 | 1/2007 | Matsuura et al. |
| 7,206,630 | B1 | 4/2007 | Tarler |
| 7,297,119 | B2 | 11/2007 | Westbrook et al. |
| 7,559,903 | B2 | 7/2009 | Moussavi et al. |
| D619,618 | S | 7/2010 | Ridgeway |
| D620,026 | S | 7/2010 | Ridgeway |
| 7,806,831 | B2 | 10/2010 | Lavie et al. |
| 8,021,299 | B2 | 9/2011 | Miesel et al. |
| 8,285,356 | B2 | 10/2012 | Bly et al. |
| D675,648 | S | 2/2013 | Self et al. |
| 8,545,416 | B1 | 10/2013 | Kayyali et al. |
| 8,591,430 | B2 | 11/2013 | Amurthur et al. |
| 8,688,190 | B2 | 4/2014 | Libbus et al. |
| 8,718,752 | B2 | 5/2014 | Libbus et al. |
| 8,764,653 | B2 | 7/2014 | Kaminska et al. |
| 8,790,257 | B2 | 7/2014 | Libbus et al. |
| 8,790,259 | B2 | 7/2014 | Katra et al. |
| 9,186,083 | B2 | 11/2015 | Osvath |
| 9,364,155 | B2 | 6/2016 | Bardy et al. |
| 9,414,785 | B2 | 8/2016 | Nagata et al. |
| 9,816,799 | B2 | 11/2017 | Keller et al. |
| 9,844,338 | B2 | 12/2017 | Abir |
| 10,531,832 | B2 | 1/2020 | Reuveny |
| 10,531,833 | B2 | 1/2020 | Reuveny et al. |
| D919,660 | S | 5/2021 | Gao et al. |
| 11,471,106 | B2 | 10/2022 | Reuveny et al. |
| 11,510,622 | B2 | 11/2022 | Reuveny |
| 11,596,354 | B2 | 3/2023 | Reuveny et al. |
| 2001/0031993 | A1 | 10/2001 | Salo et al. |
| 2002/0040192 | A1 | 4/2002 | Prutchi |
| 2002/0057202 | A1 | 5/2002 | Luzon |
| 2002/0130673 | A1 | 9/2002 | Pelrine et al. |
| 2003/0199945 | A1 | 10/2003 | Ciulla |
| 2006/0282001 | A1 | 12/2006 | Noel et al. |
| 2007/0167879 | A1 | 7/2007 | Cochran |
| 2007/0276196 | A1 | 11/2007 | Donaldson et al. |
| 2007/0293781 | A1 | 12/2007 | Sims et al. |
| 2008/0001735 | A1 | 1/2008 | Tran |
| 2008/0094226 | A1 | 4/2008 | O'Shea et al. |
| 2008/0288026 | A1 | 11/2008 | Cross et al. |
| 2008/0319277 | A1 | 12/2008 | Bradley |
| 2009/0076344 | A1 | 3/2009 | Libbus et al. |
| 2009/0076364 | A1 | 3/2009 | Libbus et al. |
| 2009/0182204 | A1 | 7/2009 | Semler et al. |
| 2010/0056882 | A1 | 3/2010 | Moore et al. |

| | | | |
|---|---|---|---|
| 2010/0228315 | A1 | 9/2010 | Nielsen |
| 2010/0317932 | A1 | 12/2010 | Ukawa |
| 2010/0328075 | A1 | 12/2010 | Rahamim et al. |
| 2011/0098549 | A1 | 4/2011 | Bar Hayim et al. |
| 2011/0270049 | A1 | 11/2011 | Katra et al. |
| 2011/0288447 | A1 | 11/2011 | Cochran |
| 2012/0242501 | A1 | 9/2012 | Tran et al. |
| 2012/0277549 | A1 | 11/2012 | Libbus et al. |
| 2013/0041235 | A1 | 2/2013 | Rogers et al. |
| 2013/0060098 | A1 | 3/2013 | Thomsen et al. |
| 2013/0123654 | A1 | 5/2013 | Rahamim et al. |
| 2013/0165809 | A1 | 6/2013 | Abir |
| 2013/0245388 | A1 | 9/2013 | Rafferty et al. |
| 2013/0247914 | A1 | 9/2013 | Truschel et al. |
| 2013/0281815 | A1 | 10/2013 | Varadan |
| 2014/0128711 | A1 | 5/2014 | Banet et al. |
| 2014/0128712 | A1 | 5/2014 | Banet et al. |
| 2014/0128713 | A1 | 5/2014 | Banet et al. |
| 2014/0128714 | A1 | 5/2014 | Banet et al. |
| 2014/0128715 | A1 | 5/2014 | Banet et al. |
| 2014/0128757 | A1 | 5/2014 | Banet et al. |
| 2014/0171762 | A1 | 6/2014 | Leboeuf et al. |
| 2014/0276168 | A1 | 9/2014 | Vissapragada et al. |
| 2014/0296808 | A1 | 10/2014 | Curran et al. |
| 2014/0330088 | A1 | 11/2014 | Libbus et al. |
| 2015/0031964 | A1 | 1/2015 | Bly et al. |
| 2015/0087922 | A1 | 3/2015 | Bardy et al. |
| 2015/0122018 | A1 | 5/2015 | Yuen |
| 2015/0143601 | A1 | 5/2015 | Longinotti-Buitoni et al. |
| 2015/0173672 | A1 | 6/2015 | Goldstein |
| 2015/0223708 | A1 | 8/2015 | Richards et al. |
| 2015/0223755 | A1 | 8/2015 | Abir |
| 2015/0335288 | A1 | 11/2015 | Toth et al. |
| 2015/0351690 | A1 | 12/2015 | Toth et al. |
| 2016/0066788 | A1 | 3/2016 | Tran et al. |
| 2016/0089031 | A1 | 3/2016 | Hu |
| 2016/0213263 | A1 | 7/2016 | Felix et al. |
| 2016/0240061 | A1 | 8/2016 | Li et al. |
| 2016/0270700 | A1 | 9/2016 | Baxi et al. |
| 2016/0287122 | A1 | 10/2016 | Heneghan |
| 2016/0287177 | A1 | 10/2016 | Huppert et al. |
| 2016/0291603 | A1 | 10/2016 | Chin et al. |
| 2016/0296166 | A1 | 10/2016 | Bardy et al. |
| 2016/0302706 | A1 | 10/2016 | Richards et al. |
| 2016/0367164 | A1 | 12/2016 | Felix et al. |
| 2017/0056682 | A1 | 3/2017 | Kumar et al. |
| 2017/0071533 | A1 | 3/2017 | Warren et al. |
| 2017/0086684 | A1 | 3/2017 | Xue et al. |
| 2017/0112422 | A1 | 4/2017 | Hatch |
| 2017/0156662 | A1 | 6/2017 | Goodall et al. |
| 2017/0164866 | A1 | 6/2017 | Rafferty et al. |
| 2017/0164876 | A1 | 6/2017 | Hyde et al. |
| 2017/0176167 | A1 | 6/2017 | Keller et al. |
| 2017/0188975 | A1 | 7/2017 | Banet et al. |
| 2017/0231490 | A1 | 8/2017 | Toth et al. |
| 2017/0238833 | A1 | 8/2017 | Felix et al. |
| 2017/0325524 | A1 | 11/2017 | Hyde et al. |
| 2017/0325525 | A1 | 11/2017 | Hyde et al. |
| 2017/0326013 | A1 | 11/2017 | Hyde et al. |
| 2017/0354372 | A1 | 12/2017 | Varadan et al. |
| 2017/0354374 | A1 | 12/2017 | Pepin et al. |
| 2018/0000347 | A1 | 1/2018 | Perez et al. |
| 2018/0020982 | A1 | 1/2018 | Elsherbini et al. |
| 2018/0138616 | A1 | 5/2018 | Dumont |
| 2018/0199884 | A1 | 7/2018 | Huppert et al. |
| 2018/0220962 | A1 | 8/2018 | Palley et al. |
| 2018/0249767 | A1 | 9/2018 | Begriche et al. |
| 2018/0249950 | A1 | 9/2018 | Bardy et al. |
| 2018/0289322 | A1 | 10/2018 | Abir |
| 2018/0293472 | A1 | 10/2018 | Fastert et al. |
| 2019/0008450 | A1 | 1/2019 | Gurievsky et al. |
| 2019/0046084 | A1 | 2/2019 | Kilcran et al. |
| 2019/0046087 | A1 | 2/2019 | Kuller |
| 2019/0209028 | A1 | 7/2019 | Baxi |
| 2019/0223749 | A1 | 7/2019 | Toth et al. |
| 2019/0239799 | A1 | 8/2019 | Bardy et al. |
| 2019/0373963 | A9 | 12/2019 | Longinotti-Buitoni et al. |
| 2020/0128670 | A1 | 4/2020 | Chong Rodriguez et al. |
| 2020/0222707 | A1 | 7/2020 | Kumar et al. |

(56)  References Cited

U.S. PATENT DOCUMENTS

| | | | |
|---|---|---|---|
| 2020/0315488 A1 | 10/2020 | Rogers et al. |
| 2020/0315524 A1 | 10/2020 | Bardy et al. |
| 2020/0375548 A1 | 12/2020 | Quinlan et al. |
| 2020/0390394 A1 | 12/2020 | Varadan |
| 2021/0195732 A1 | 6/2021 | Longinotti-Buitoni et al. |
| 2021/0213296 A1 | 7/2021 | Kumar et al. |
| 2021/0298173 A1 | 9/2021 | Gisby et al. |
| 2021/0330252 A1 | 10/2021 | Bardy et al. |
| 2021/0353228 A1 | 11/2021 | Palley et al. |
| 2022/0386960 A1 | 12/2022 | Reuveny et al. |
| 2023/0043076 A1 | 2/2023 | Reuveny |

FOREIGN PATENT DOCUMENTS

| | | | |
|---|---|---|---|
| CN | 106859598 A | 6/2017 |
| TW | D204247 S | 4/2020 |
| WO | WO-2014055994 A1 | 4/2014 |
| WO | WO-2015135368 A1 | 9/2015 |
| WO | WO-2017115376 A1 | 7/2017 |
| WO | WO-2017201419 A1 | 11/2017 |
| WO | WO-2019074787 A1 | 4/2019 |

OTHER PUBLICATIONS

Dreem—Sleep Pioneers, Building the healthcare of tomorrow, one night at a time, retrieved on Jun. 15, 2021 from https://dreem.com/, 23 pages.
Extended European Search Report dated Mar. 3, 2022 for European Application No. 18865600.3, 12 pages.
Final Office Action for U.S. Appl. No. 16/705,820 mailed on Jun. 22, 2022, 9 pages.
Final Office Action for U.S. Appl. No. 16/705,806, filed Jun. 8, 2022, 10 pages.
Intellibed, Introducing Intellibed Sleep Genius ™, retrieved on Jun. 15, 2021 from https://www.intellibed.com/sleep-genius-smart-base/, 9 pages.

International Search Report and Written Opinion mailed Feb. 14, 2019 for International Application No. PCT/US2018/054592, 16 pages.
Invitation to Pay Additional Fees mailed Nov. 27, 2018 for International Application No. PCT/US2018/054592, 2 pages.
Liu, S. & Ostadabbas, S., "A Vision-Based System for In-Bed Posture Tracking," 2017 IEEE International Conference on Computer Vision Workshops (ICCVW), pp. 1373-1382 (2017).
Majumder, S. et al., "Wearable Sensors for Remote Health Monitoring," Sensors 2017, www.mdpi.com/journal/sensors, 45 pages.
Non Final Rejection Office Action for U.S. Appl. No. 17/888,779, mailed on Oct. 31, 2022, 7 pages.
Non-Final Office Action for U.S. Appl. No. 16/705,806, dated Feb. 22, 2022, 13 pages.
Non-Final Office Action mailed Jul. 30, 2019 for U.S. Appl. No. 16/152,649, 13 pages.
Non-Final Office Action mailed Jun. 21, 2019 for U.S. Appl. No. 16/404,825, 14 pages.
Non-Final Office Action mailed Mar. 1, 2022 for U.S. Appl. No. 16/705,820, 10 pages.
Office Action for Chinese Application No. CN201880065458.1 dated Nov. 24, 2022, 13 pages.
Pillow Sleep Cycle Tracker for Apple Watch, Sleeping Better Made Simple, retrieved on Jun. 15, 2021 from https://pillow.app/, 29 pages.
Sleep Cycle, Sleep Tracker, Monitor & Alarm Clock, retrieved on Jun. 15, 2021 from https://sleepcycle.com, 10 pages.
Sleep Score: Best Sleep Monitoring App, retrieved on Jun. 15, 2021 from ttps://www.sleepscore.com/sleepscore- app/, 4 pages.
Sleeptracker-A1®, The PaaS Sleep Platform by Fullpower-A 1, retrieved on Jun. 15, 2021 from https://www.sleeptracker.com/, 55 pages.
Wang, Y. -K. et al., "Unobtrusive Sleep Monitoring Using Movement Activity by Video Analysis," Electronics, 8:812 (2019), 17 pages; doi:10.3390/electronics8070812.
Office Action and Search Report for Chinese Application No. CN201880065458.1 dated May 9, 2023, with English translation, 15 pages.
Office Action for Chinese Application No. CN201880065458.1 dated Oct. 27, 2023, with English translation, 14 pages.

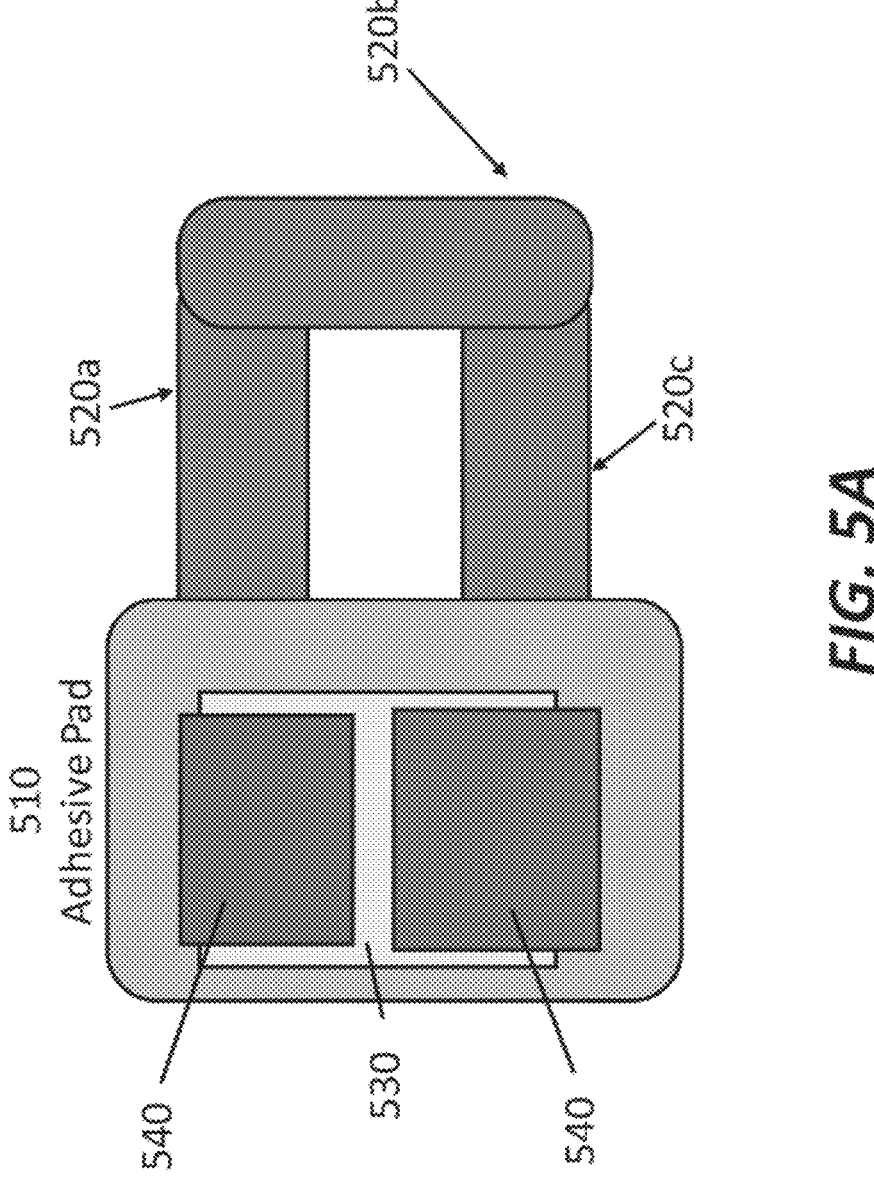
*FIG. 5A*

570
Circuitry

530
Power

Stretchable adhesive pad 510

520
Flexible conductor

570/530
Circuitry/ Power

Stretchable adhesive pad 510

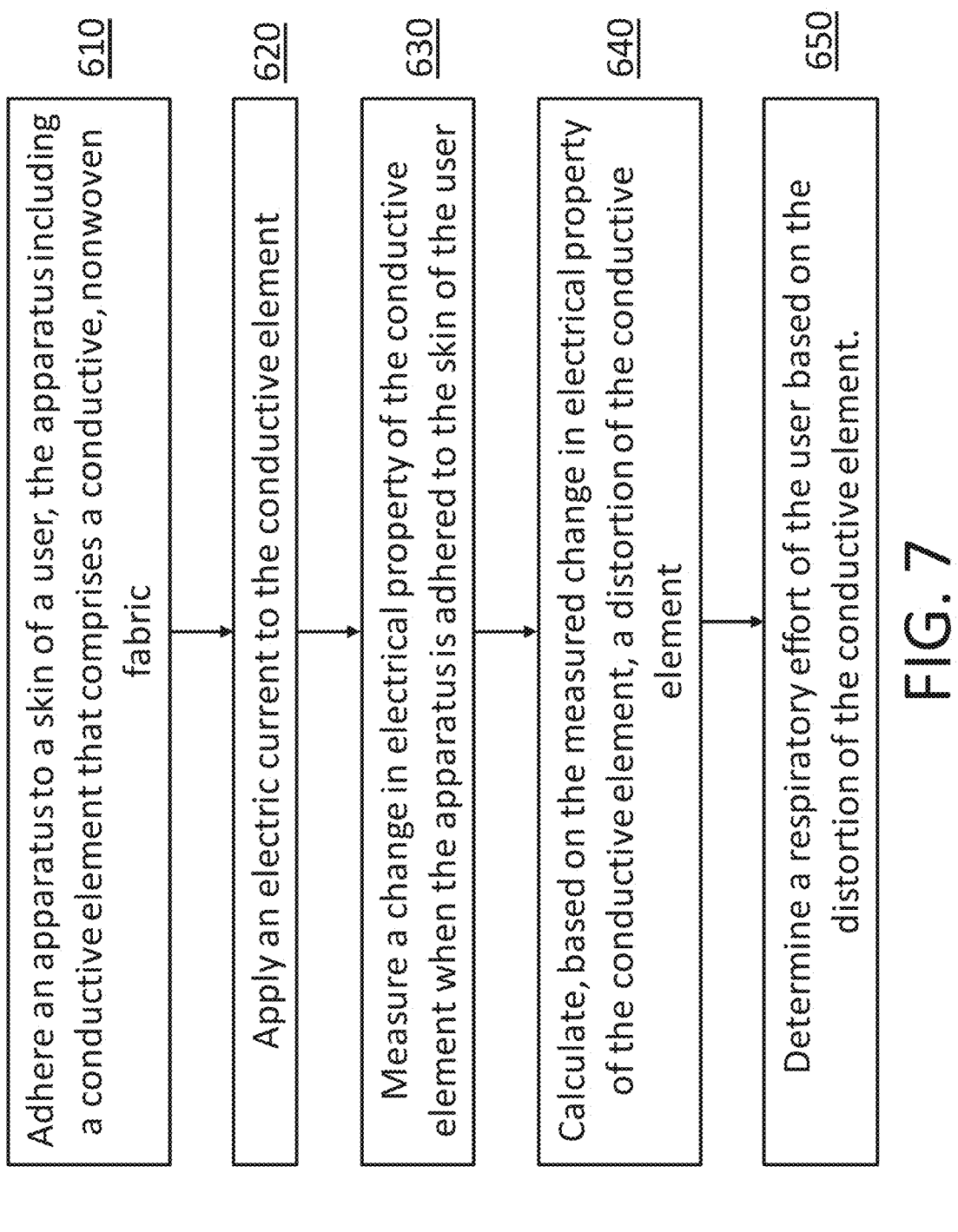

Adhere an apparatus to a skin of a user, the apparatus including a conductive element that comprises a conductive, nonwoven fabric    610

Apply an electric current to the conductive element    620

Measure a change in electrical property of the conductive element when the apparatus is adhered to the skin of the user    630

Calculate, based on the measured change in electrical property of the conductive element, a distortion of the conductive element    640

Determine a respiratory effort of the user based on the distortion of the conductive element.    650

SYSTEMS, APPARATUS, AND METHODS FOR DETECTION AND MONITORING OF CHRONIC SLEEP DISORDERS

CROSS-REFERENCE TO RELATED APPLICATION

This application is a Continuation of U.S. patent application Ser. No. 16/705,806, filed Dec. 6, 2019, now U.S. Pat. No. 11,510,662, titled "SYSTEMS, APPARATUS, AND METHODS FOR DETECTION AND MONITORING OF CHRONIC SLEEP DISORDERS," which is a Continuation of U.S. patent application Ser. No. 16/404,825, filed on May 7, 2019 and titled "SYSTEMS, APPARATUS, AND METHODS FOR DETECTION AND MONITORING OF CHRONIC SLEEP DISORDERS," now U.S. Pat. No. 10,531,833, which is a Continuation of U.S. patent application Ser. No. 16/152,649, filed on Oct. 5, 2018 and titled "SYSTEMS, APPARATUS, AND METHODS FOR DETECTION AND MONITORING OF CHRONIC SLEEP DISORDERS," now U.S. Pat. No. 10,531,832, which claims the priority and benefit of U.S. Provisional Patent Application No. 62/569,783, filed on Oct. 9, 2017 and titled "DEVICE AND METHOD FOR DETECTION AND MONITORING OF CHRONIC SLEEP DISORDERS," the disclosures of each of which are hereby incorporated by reference in their entireties.

TECHNICAL FIELD

The present disclosure relates generally to systems, apparatus, and methods for monitoring a sleep parameter of a user, and more particularly to sensor-based detection and monitoring of chronic sleep disorders in a home setting.

BACKGROUND

Millions of people suffer from various forms of chronic sleep disorders (CSDs), including insomnia, sleep apnea, and periodic limb movement disorder (PLMD). CSDs may account for billions of dollars of lost work productivity. For example, sleep apnea alone has been estimated to cost workplaces $150 billion annually.

While the number of patients seeking help for CSDs has grown in recent years, a majority of those suffering from a CSD remain undiagnosed. A significant factor that disincentives potential patients from seeking help is the high cost. Professional assessments of sleep, such as administering a polysomnogram, usually engage a patient to spend a night at a "sleep lab" to monitor various factors while the patient is sleeping, such as brain activity, eye movements, heart rate, and blood pressure. These assessments typically involve expensive equipment, and can cost upwards of $5,000 per night.

While home sleep test designed to be self-administered by patients do exist, many such tests still use elaborate equipment that is assembled by the users (e.g. home assembly), which can be frustrating, and can be uncomfortable to wear. Many such tests also attach multiple parts to a patient's body, including an oxygen monitor, nasal tubes, and chest straps. Additionally, these tests are often inaccurate. Therefore, multiple attempts are usually conducted to capture meaningful data. Furthermore, the recorded data in these tests is often sent to physicians for analysis, thereby adding a logistical obstacle to the diagnosis and monitoring of a potential CSD.

SUMMARY

Systems, apparatus, and methods are disclosed for detecting and monitoring sleep parameters of a user. In some embodiments, an apparatus for monitoring a sleep parameter of a user includes an adhesive pad configured to conform to a surface of the user and at least one flexible element coupled to the adhesive pad. The flexible element can be configured to exhibit a modified electrical property (e.g., resistance, resistivity, reactance, impedance, etc.) in response to an applied force. The apparatus also includes a power source electrically coupled to the flexible element. The flexible element can include a conductive fabric. The apparatus also includes an electrical circuit electrically coupled to the power source and the flexible element. The electrical circuit is configured to detect, during use, a change in an electrical property of the flexible element. In some embodiments, the flexible element is a piezoresistive element In some embodiments, a system for monitoring a sleep parameter of a user includes a portable electronic device, a first patch sensor, and a second patch sensor. The first patch sensor includes a first adhesive pad configured to conform to a first surface of the user, a first flexible conductive strip coupled to the first adhesive pad, and a first electrical circuit electrically coupled to the first flexible conductive strip. The first flexible conductive strip is configured to exhibit a modified electrical property in response to an applied force. The first electrical circuit is configured to detect, during use, a change in an electrical property of the first flexible conductive strip. The second patch sensor includes a second adhesive pad configured to conform to a second surface of the user different from the first surface of the user, a second flexible conductive strip coupled to the second adhesive pad, and a second electrical circuit electrically coupled to the second flexible conductive strip. The second flexible conductive strip is configured to exhibit a modified electrical property in response to an applied force. The second electrical circuit is configured to detect, during use, a change in an electrical property of the second flexible conductive strip. Each of the first electrical circuit and the second electrical circuit is configured to transmit electrical property change data to the portable electronic device for determination of the sleep parameter.

In some embodiments, a method includes adhering an apparatus to a skin of a user. The apparatus includes a conductive element configured to exhibit a modified electrical property in response to an applied force, the conductive element including a conductive fabric (e.g., a woven or nonwoven fabric). The method also includes applying an electric current to the conductive element and measuring a change in electrical property of the conductive element when the apparatus is adhered to the skin of the user. The method further includes calculating, based on the measured change in electrical property of the conductive element, a distortion of the conductive element, and determining a respiratory effort of the user based on the distortion of the conductive element.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 5A is a schematic illustration of an apparatus for monitoring a sleep parameter of a user, in accordance with some embodiments.

FIG. 7 is a flowchart illustrating a method of monitoring a respiratory effort of a user in accordance with some embodiments.

DETAILED DESCRIPTION

The present disclosure describes systems, apparatus, and methods for monitoring a sleep parameter of a user, and more particularly to detection and monitoring of chronic sleep disorders in a home setting using one or more flexible elements, which may be conductive and/or exhibit modified electrical properties in response to an applied force.

To address the challenges in conventional methods of monitoring sleep disorders, apparatuses, systems, and methods described herein employ a flexible element to monitor sleep parameters, such as respiratory effort, of a user. In some embodiments, an apparatus for monitoring a sleep parameter of a user includes an adhesive pad configured to conform to a surface of the user. A flexible element is coupled to the adhesive pad and includes a conductive material, such as a conductive, nonwoven fabric or other textile and/or a conductive polymer. The apparatus also includes a power source electrically coupled to the flexible element and an electrical circuit electrically coupled to the power source and the flexible element. The electrical circuit is configured to detect, during use, a change in an electrical property of the flexible element. The electrical property of the flexible element can include, for example, resistance, reactance, impedance, or any other suitable property.

During use, the adhesive pad can be attached to the skin of the user during use (e.g., on the torso of the user). Breathing of the user can cause the skin to compress or stretch, thereby compressing and stretching the flexible element accordingly. The compression and stretching of the flexible element in turn changes its electrical property, which can be measured by the electrical circuit. In this manner, the breathing of the user can be monitored by monitoring the electrical property of the element.

In some embodiments, devices (e.g., respiratory monitor, sleep monitor, sleep disorder detector, etc.) based on the approach described herein can be configured as a patch that can be conveniently worn by the user or attached to the user without causing excessive discomfort to the user. Therefore, the breathing and/or sleep of the user can be readily monitored in a home setting. In some embodiments, the measurements of the device can be transmitted to another device, such as a computer, a smartphone, or a tablet, among others, and the user can conveniently review the measurements therein.

Figure 1A:
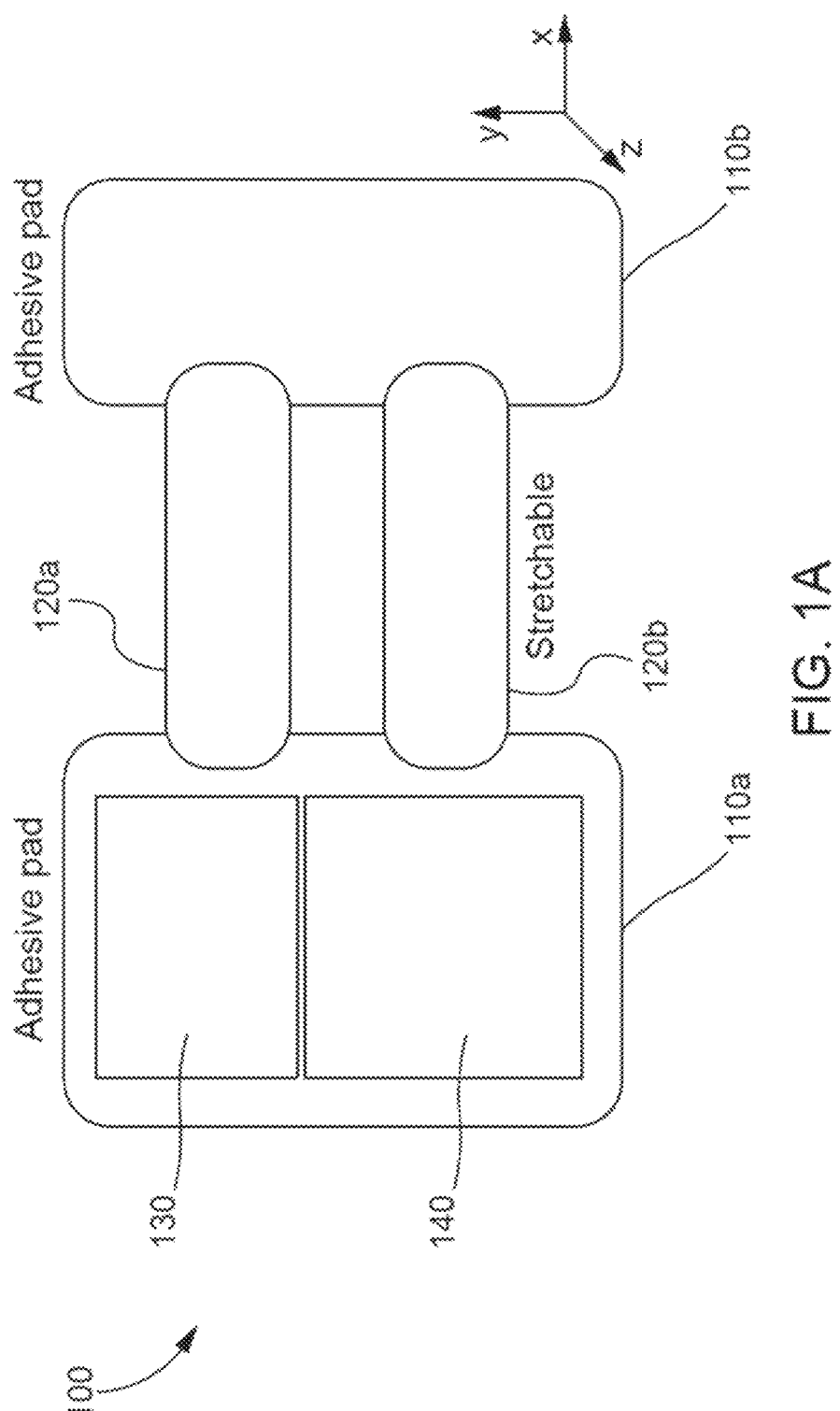
FIGS. 1A-1C show a schematic illustration of an apparatus for monitoring a sleep parameter of a user, in accordance with some embodiments.
Figure 1C:
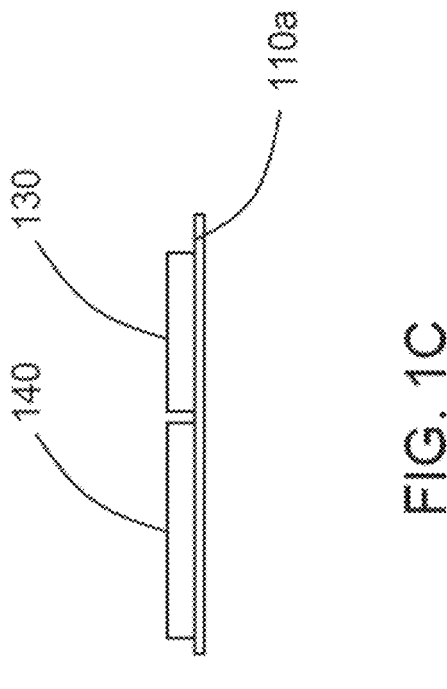
Figure 1B:
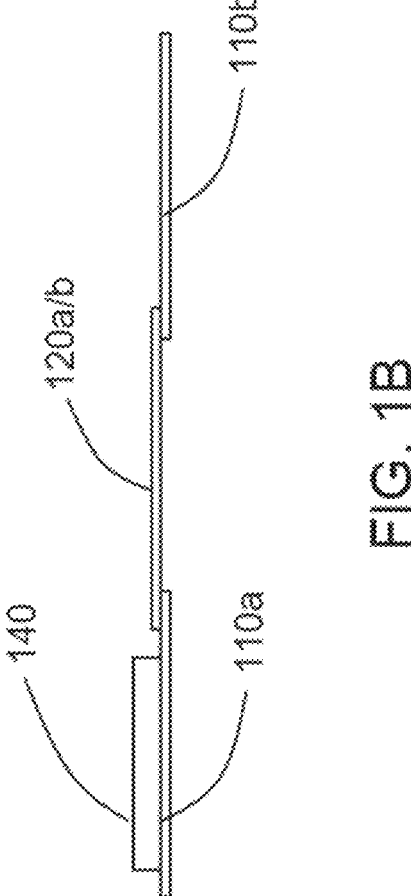

FIGS. 1A-1C show a schematic illustration of an apparatus 100 for monitoring a sleep parameter of a user, according to embodiments. FIG. 1A shows a top view of the apparatus 100, FIG. 1B shows a side view of the apparatus 100, and FIG. 1C shows a back view of the apparatus 100.

The apparatus 100 includes a first adhesive pad 110a and a second adhesive pad 110b (collectively referred to as adhesive pad 110) connected by a pair of flexible elements 120a and 120b (collectively referred to as element 120). One or both of flexible elements 120a and 120b can be configured to exhibit a modified electrical parameter (e.g., resistance, reactance, capacitance) in response to an applied external force (e.g., pressure, compression, tension, etc.). The adhesive pad 110 can be conformally attached to the surface of the user (e.g., on the skin, see FIGS. 5A-5C) and substantially secured to the surface of the user during use. When the user breathes (i.e., inhales and/or exhales), the area of the user's surface can change accordingly, thereby causing a change in the distance between the first adhesive pad 110a and the second adhesive pad 110b. In other words, there can be an elongation along an axis extending from the first adhesive pad 110a to the second adhesive pad 110b (or, in the case of a single adhesive pad, an elongation of the single adhesive pad). In response, the dimension of the flexible element 120 (e.g., length along the x direction) also changes, inducing a change in the electrical property of the flexible element 120.

The apparatus 100 also includes a power source 130 electrically coupled to the flexible element 120 and an electrical circuit 140 electrically coupled to the power source 130 and the flexible element 120. The electrical circuit 140 is configured to detect, during use, the change of the electrical property of the flexible element 120. In some embodiments, the electrical circuit 140 can further include a processor (see, e.g., FIG. 2) to process the data representing the change of the electrical property of the flexible element 120 so as to calculate the sleep parameter of the user (or any other respiratory parameter).

FIGS. 1A-1C show that the apparatus 100 includes two adhesive pads, 110a and 110b. In some embodiments, the apparatus 100 can include a single adhesive pad 110 see, e.g., FIG. 5 and corresponding description below), and the element 120 can be conformally disposed on the adhesive pad 110. In addition, the adhesive pad 110 can also be flexible such that the compression/stretching of the skin can cause the adhesive pad 110 to compress/stretch accordingly, thereby inducing a change to an electrical property of the element 120.

In some embodiments, the apparatus 100 includes more than two adhesive pads 110a and 110b. For example, a third adhesive pad (not shown) can be included in the apparatus 100 and coupled to the first adhesive pad 110a via one or two additional elements (not shown). The first adhesive pad 110a and the third adhesive pad can form an axis along they direction, and the long edges of the additional element(s) are also long they direction. In these instances, the compression and/or stretching of the user's skin along they direction can also be measured by the apparatus 100. In some embodiments, the apparatus 100 includes more than three adhesive pads (e.g., 4 adhesive pads, 5 adhesive pads, or more).

The flexible element 120 can include any suitable conductive and/or piezoresistive material. Piezoresistivity (or "piezoresistive behavior"), as used herein, refers to the property of a material (including, but not limited to, conductors, metals, and semiconductors) exhibiting or undergoing a change in an electrical property (e.g., resistance, resistivity, reactance, and/or impedance) when an external, applied mechanical force is applied and a corresponding compression, tension, or strain is induced therein. In some embodiments, the element 120 includes a semiconductor (e.g., one or more polymer-based semiconductors, such as poly(3,4-ethyl enedioxythiophene) polystyrene (PEDOT: PSS), one or more organic semiconductors, etc.). In some embodiments, the element 120 can include a conductor material.

In some embodiments, the element 120 includes a conductive rubber or a conductive elastomer. In some embodiments, the element 120 includes a piezoelectric polymer, such as polyvinylidene fluoride or polyvinylidene difluoride (PVDF) and its derivatives. In some embodiments, the element 120 includes a stretchable conductive fabric. The fabric can be, for example, knitted or woven. In some embodiments, the element 120 includes conductive threads or particles disposed on, or interweaved or embedded in, a non-conductive fabric.

In some embodiments, the element 120 includes a nonwoven fabric. As used herein, a nonwoven fabric refers to a sheet or a web structure bonded together by entangling fiber or filaments mechanically, thermally, or chemically. The nonwoven fabric can be flat, porous, and can be made directly from separate fibers. In addition, a nonwoven fabric is not made by weaving or knitting and usually does not involve converting the fibers to yarn. The fiber in the nonwoven fabric that forms the element 120 can include any of the materials described above.

In some embodiments, the element 120 includes a fabric that has a substrate material coated with a conductive material. For example, individual fibers within the fabric (or yarn, if the fabric if woven or knitted) can be completely and uniformly coated with a conductive polymer, such as doped polypyrrole (PPY). The substrate material can include, for example, polyester, nylon, and glass. More details and examples about this fabric can be found in U.S. Pat. No. 5,833,884A, entitled "Method of enhancing the stability of conductive polymers," the disclosure of which is hereby incorporated by reference in its entirety.

In some embodiments, the length of the element 120 (i.e., dimension along the x direction as illustrated in FIG. 1A) is about 1 mm to about 200 mm (e.g., about 1 mm, about 5 mm, about 10 mm, about 20 mm, about 30 mm, about 50 mm, about 100 mm, or about 200 mm, including any values and sub-ranges in between, e.g., about 5 mm to about 200 mm, or about 10 mm to about 200 mm). In some embodiments, the width of the element 120 (i.e., dimension along the y direction) is about 1 mm to about 30 mm (e.g., about 1 mm, about 5 mm, about 10 mm, about 15 mm, about 20 mm, about 25 mm, or about 30 mm, including any values and sub ranges in between, e.g., about 5 mm to about 30 mm). In some embodiments, the thickness of the element 120 (i.e. dimension along the z direction) can be about 0.1 mm to about 5 mm (e.g., about 0.1 mm, about 0.5 mm, about 1 mm, about 2 mm, about 3 mm, about 4 mm, or about 5 mm, including any values and sub ranges in between, e.g., about 0.5 mm to about 5 mm). As used herein, the phrase "about" refers to the range of 10% within a reference value. For example, about 10 mm refers to the range of 9 mm to 11 mm. In some embodiments, the element 120 exhibits, during use, a linear (or substantially linear) relationship between $\Delta L/L$ and $\Delta R/R$, where L is an initial length of the element, $\Delta L$ is the relative change in length of the element in response to an applied tension/compression, R is an initial resistance of the element, and $\Delta R$ is the relative change in resistance of the element in response to the applied tension/compression.

The apparatus 100 shown in FIG. 1A includes two elements 120a and 120b. In some embodiments, the apparatus 100 can include a single element 120 connecting the two adhesive pads 110a and 110b. In some embodiments, the apparatus 100 can include three elements. In some embodiments, the apparatus 100 can include more than three elements. Increasing the number of elements in the apparatus 100 can, for example, increase a sensing sensitivity of the apparatus 100, particularly if they align or substantially align with a stretch axis of the apparatus 100.

In some embodiments, the power source 130 can include a battery. In some embodiments, the power source 130 can be include a solar cell. In some embodiments, the power source 130 can include a capacitor. In some embodiments, the power source 130 can include a supercapacitor. In some embodiments, the power source 130 can be rechargeable. In some embodiments, the power source 130 can be recharged via wireless energy transfer (e.g., via inductive charging or resonant wireless charging).

The electrical circuit 140 in the apparatus 100 is configured to measure the change in the electrical property of the element 120. In some embodiments, the electrical circuit 140 can include a resistivity meter to measure the resistivity (and/or the change of resistivity) of the element 120. In some embodiments, the electrical circuit 140 can include an LCR meter to measure the inductance, capacitance, and/or resistance of the element 120.

In some embodiments, the electrical circuit 140 can be integrated into a chip to increase the compactness of the apparatus 100. In some embodiments, the electrical circuit 140 can include a processor to analyze the data acquired from measurements. The electrical circuit 140 can further include a memory to store processor executable instructions so as to instruct the processor to process the data (and/or implement any other functions). In some embodiments, the electrical circuit 140 can also include a communication interface (see, e.g., FIG. 2) to communicate with external devices, such as a computer, a smartphone, or a tablet. In some embodiments, the external device can be a portable electronic device. In some embodiments, the external device can be substantially fixed at a certain location, such as a network server.

In operation, the change in the electrical property of the element 120 can be measured as long as the dimension (e.g., length along the x direction) of the element 120 changes. In some embodiments, the change in the electrical property of the element 120 can be measured when the element 120 transitions from one state to another state. For example, the element 120 can have three states: neutral stress state, compressed state, and tensile state. Without being bound by any particular theory or mode of operation, the neutral stress state refers to the equilibrium state in which the element 120 is not being stretched or compressed. The compressed state refers to the state in which the element 120 is experiencing compressive stress. The tensile state refers to the state in which the element 120 is under a stretching force.

In some embodiments, the element 120 can be in the neutral stress state before being coupled to the user, i.e. the element 120 is not compressed or stretched before use. When coupled to the user, the element 120 can be configured into the compressed state. During use, the breathing of the user can cause the element 120 to transition from one state to another. For example, the inhalation of the user can cause the element 120 to transition from the compressed state to the tensile state (via the neutral stress state), and the exhalation of the user can cause the element 120 to transition back to the compressed state (via the neutral stress state).

In other embodiments, the element 120 can be in a compressed state before being coupled to the user, and when coupled to the user, the element 120 can be further compressed and/or stretched. During use, the breathing of the user can cause the element 120 to transition from one state to another. For example, the inhalation of the user can cause the element 120 to transition from the compressed state to a tensile state (via the neutral stress state), and the exhalation of the user can cause the element 120 to transition back to the compressed state (via the neutral stress state). Alternatively, the inhalation of the user can cause the element 120 to transition from the compressed state to a more compressed state, and the exhalation of the user can cause the element 120 to transition back to the previous compressed state. Alternatively, the inhalation of the user can cause the element 120 to transition from the compressed state to a less compressed state, and the exhalation of the user can cause the element 120 to transition back to the previous compressed state.

In still other embodiments, the element 120 can be in a tensile (stretched) state before being coupled to the user, and when coupled to the user, the element 120 can be further compressed and/or stretched. During use, the breathing of the user can cause the element 120 to transition from one state to another. For example, the inhalation of the user can cause the element 120 to transition from the tensile state to a compressed state (via the neutral stress state), and the exhalation of the user can cause the element 120 to transition back to the tensile state (via the neutral stress state). Alternatively, the inhalation of the user can cause the element 120 to transition from the tensile state to a more tensile state, and the exhalation of the user can cause the element 120 to transition back to the previous tensile state. Alternatively, the inhalation of the user can cause the element 120 to transition from the tensile state to a less tensile state, and the exhalation of the user can cause the element 120 to transition back to the previous tensile state.

In some embodiments, the electrical circuit 140 is configured to measure the electrical property of the element 120 in each state and then calculate the difference in the electrical property of the piezoelectric element 120 between the different states. For example, during inhalation of the user, the electrical circuit 140 can be configured to measure the difference in the electrical property of the element 120 when the element 120 transitions from the compressed state to the neutral stress state. The electrical circuit 140 can also be configured to measure the difference in the electrical property of the element 120 when the element 120 transitions from the neutral stress state to the tensile state. Alternatively or additionally, the electrical circuit 140 can also be configured to measure the difference in the electrical property of the element 120 when the element 120 transitions from the compressed state to the tensile state.

Similarly, during the exhalation of the user, the electrical circuit 140 can be configured to measure the difference in the electrical property of the element 120 when the element 120 transitions from the tensile state to the neutral stress state, as well as the difference in the electrical property of the element 120 when the element 120 transitions from the neutral stress state to the compressed state. Alternatively or additionally, the electrical circuit 140 can also be configured to measure the difference in the electrical property of the element 120 when the element 120 transitions from the tensile state to the compressed state.

In some embodiments, the electrical circuit 140 is configured to measure the change in the electrical property of the element 120 when the element 120 transitions from one state to another. In these instances, the electrical circuit 140 can be configured not to measure the absolute value of the electrical property of the element 120 in each state.

In some embodiments, the element 120 can transition between different degrees within the same state in response to the breathing of the user. For example, the inhalation of the user can cause the element 120 to transition from one degree of tensile state to another degree of tensile state. During this transition, the element 120 remains in the tensile state, but the dimension of the element 120 changes and accordingly the electrical property of the element 120 changes. Such a difference in the electrical property can also be used to derive the sleep parameter (or any other respiratory parameter) of the user.

In some embodiments, the dimension change of the element 120 measured by the apparatus 100 is along the x direction (as illustrated in FIG. 1A). In some embodiments, the dimension change of the element 120 measured by the apparatus can be along both the x direction and the y direction. For example, one or more additional element can be included in the apparatus 100 and configured to measure the dimension change in they direction. In some embodiments, dimension change of the element 120 measured by the apparatus 100 can also include dimension change in the z direction, i.e., perpendicular to the skin of the user, for example to detect positioning of, or pressure on, one or more portions of the apparatus 100 (e.g., on the element(s) 120).

Figure 2:
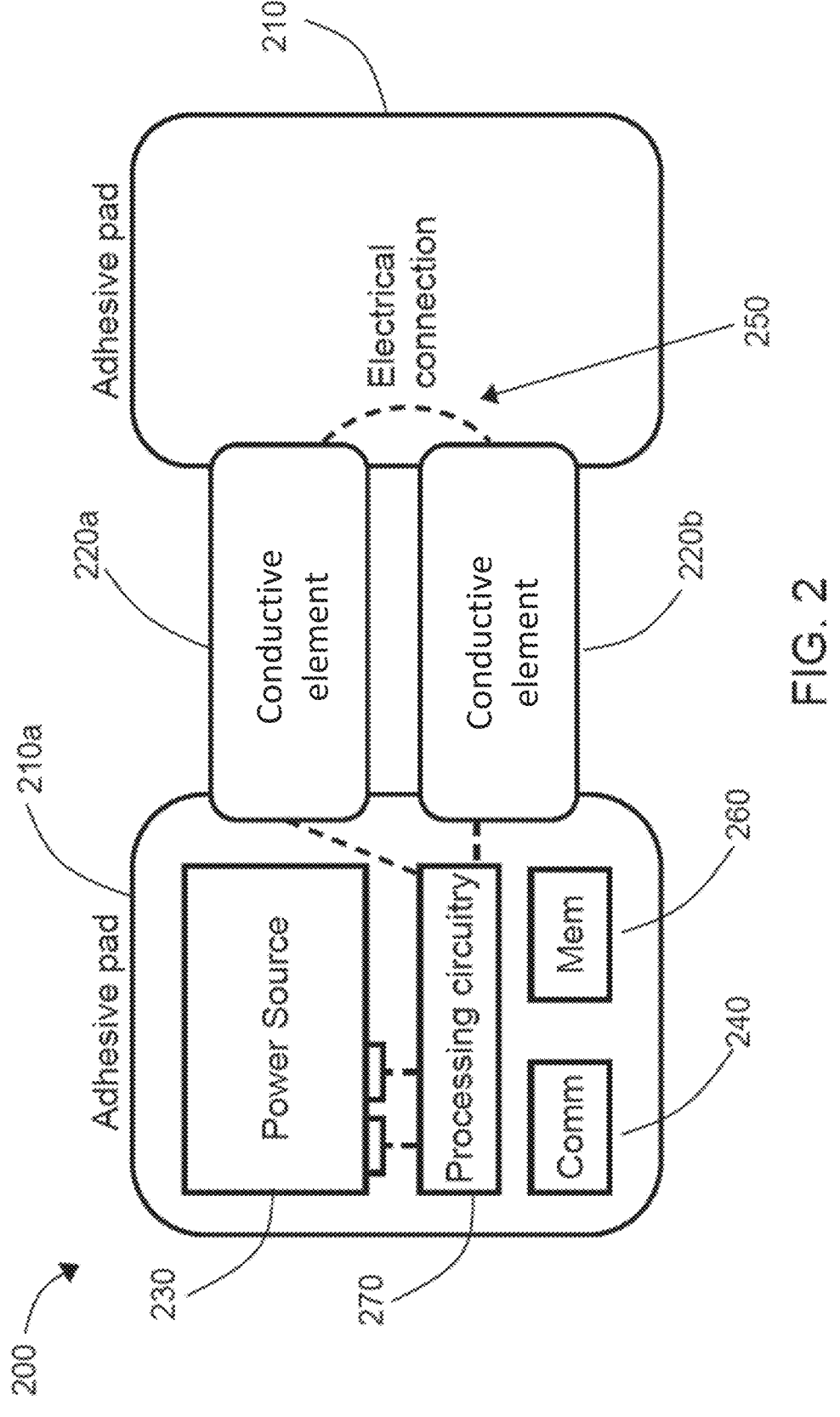
FIG. 2 shows a schematic illustration of an apparatus including a processor and a communication interface for monitoring a sleep parameter of a user, in accordance with some embodiments.

FIG. 2 shows a schematic illustration of an apparatus 200 including a processor and a communication interface for monitoring a sleep parameter of a user, in accordance with some embodiments. The apparatus 200 includes two adhesive pads 210a and 210b (collectively referred to as adhesive pad 210) connected together by a pair of flexible elements/sheets 220a and 220b (collectively referred to as element 220). In some embodiments, element 220a is a conductive element that does not exhibit piezoresistive behavior, and element 220b is an element that exhibits piezoresistive behavior. In other embodiments, both element 220a and element 220b exhibit piezoresistive behavior. Apparatuses

200 in which both element 220a and element 220b exhibit piezoresistive behavior can exhibit a greater sensing sensitivity than apparatuses 200 in which element 220a is a conductive element that does not exhibit piezoresistive behavior, and element 220b is an element that exhibits piezoresistive behavior. The element 220 can be configured to change an electrical property (e.g., resistance) in response to stress or pressure applied thereto. In addition, the two elements 220a and 220b are electrically coupled to each other via an electrical connection 250 (e.g., a wire or any other conductive link), thereby allowing electrical current to flow through the two elements 220a and 220b.

The apparatus 200 also includes a power source 230 (e.g. a battery) that is connected to a processing circuitry 270. The power source 230 is also connected to the element 220 to allow the measurement of the electrical property of the element 220. In some embodiments, the power source 230 can be in direct connection with the element 220. In some embodiments, the power source 230 can be electrically coupled to the element 220 via the processing circuitry 270.

The adhesive pad 210, the element 220, and the power source 230 can be substantially similar to the adhesive pad 110, the element 120, and the power source 130 illustrated in FIGS. 1A-1C and described above. For example, the adhesive pad 210 can include an adhesive configured to cling firmly to the skin of a user, such that when the area of a user's skin connected to the adhesive pad 210 moves, e.g., expands, contracts, rotates, and the like, relative to a starting position, a pressure or stress is applied to the element 220 spanning in between the two adhesive pads 210a and 210b.

The processing circuitry 270 is connected to a communication interface 240 that is configured to communication with another device, such as a user device. Examples of the user device can include a personal computer, a laptop, a tablet computer, a smartphone, a smart TV, a wearable computing device, or any other device capable of sending and receiving data.

The apparatus 200 also includes a memory 260 that is configured to store processor executable instructions (e.g., software). As used herein, software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed, cause the processing circuitry 270 to perform the various processes described herein. For example, the instructions stored in the memory 260 can instruct the processing circuitry 270 to process raw data acquired from the measurement of the electrical property of the element 220. The memory 260 can also be configured to store data (e.g., raw data or processed data) and allow the communication interface 240 to transmit the data to another device.

The communication interface 240 of the apparatus 200 can be any suitable module and/or device that can place the resource in communication with the apparatus 200 such as one or more network interface cards or the like. Such a network interface card can include, for example, an Ethernet port, a WiFi® radio, a Bluetooth® radio (e.g., a Bluetooth® antenna), a near field communication (NFC) radio, and/or a cellular radio. As such, the communication interface can send signals to and/or receive signals from another device. In some instances, the communication interface of the apparatus 200 can include multiple communication interfaces (e.g., a WiFi® communication interface to communicate with the one external device and a Bluetooth® communication interface to send and/or broadcast signals to another device). The memory 260 can be a random access memory (RAM), a memory buffer, a hard drive, a read-only memory (ROM), an erasable programmable read-only memory (EPROM), and/or the like.

The processing circuitry 270 can include any suitable processing device configured to run or execute a set of instructions or code (e.g., stored in the memory) such as a general-purpose processor (GPP), a central processing unit (CPU), an accelerated processing unit (APU), a graphics processor unit (GPU), an Application Specific Integrated Circuit (ASIC), and/or the like. Such processing circuitry 270 can run or execute a set of instructions or code stored in a memory associated with using a PC application, a mobile application, an internet web browser, a cellular and/or wireless communication (via a network), and/or the like.

The processing circuitry 270 can be realized as one or more hardware logic components and circuits. For example, and without limitation, illustrative types of hardware logic components that can be used include general-purpose microprocessors, microcontrollers, digital signal processors (DSPs), and the like, or any other hardware logic components that can perform calculations or other manipulations of information.

In operation, the apparatus 200 can be configured to measure the respiratory effort exerted by a user via the piezoresistive effect. The respiratory effort can be represented, for example, as a voltage (e.g., μV, mV, or V). A voltage is applied by the power source 230 across the element 220, and a certain resistance (e.g., initial resistance) is introduced. When the user's skin is expanded or contracted, the element 220 reacts by expanding or contracting, respectively, thereby inducing changes in the electrical property. Such changes are captured by the processing circuitry 270 and associated with a user movement, such as how much a user's chest is rising and falling.

The movements can be correlated to the respiratory effort or the breathing rate of a user. Analyzing the respiratory effort can reveal information about the breathing and/or sleep issues of the user. For example, it may be determined that the normal respiratory rate is about 12-16 per minute for an adult, 15-25 per minute for a child, and 20-40 per minute for an infant. Rates above or below these ranges may be determined as indication of abnormal conditions of the user. In another example, the movements can be correlated to the respiratory effort of the user, indicating possible difficulty in breathing as a result of partial or full blockage of one of the user's air paths. The respiratory effort measurement is also a useful parameter in detecting one of the most common and severe sleep disorders, sleep apnea.

Figure 3:
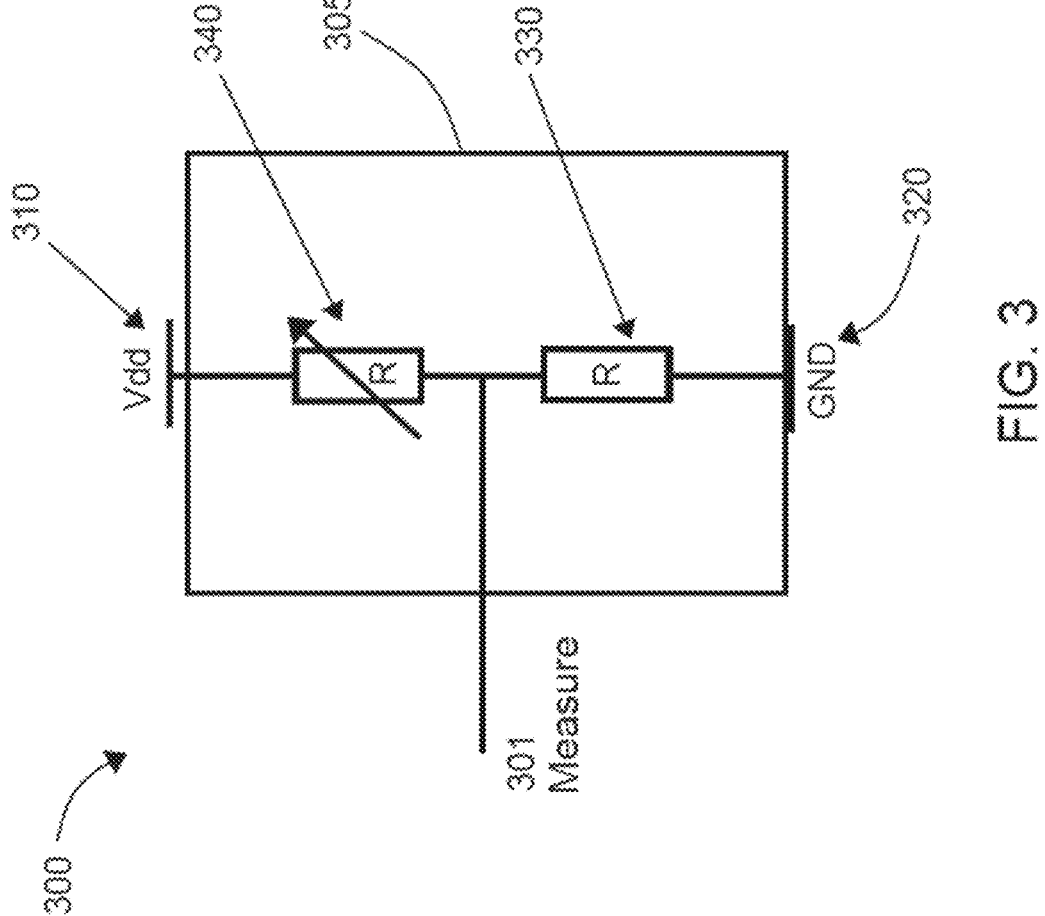
FIG. 3 illustrates a piezoresistive mechanism employed in the apparatus 100 and 200 shown in FIGS. 1A-1C and FIG. 2, respectively, in accordance with some embodiments.

FIG. 3 illustrates the piezoresistive mechanism 300 employed in the apparatus 100 and 200 shown in FIGS. 1A-1C and FIG. 2, respectively, according to embodiments. In this mechanism 300, a voltage 310 (e.g., from the power source 130 in FIG. 1A or 230 in FIG. 2), such as from a positive voltage drain ($V_{dd}$) supply, is applied across a flexible element 305 (e.g., similar to 120 in FIG. 1A or 220 in FIG. 2) to a ground connection 320. The resistance of the electrical flow changes with respect to the tension or pressure applied to element 220.

The element 305 can be described as a potentiometer resistor 340 shown in FIG. 3. In order to measure the relative change in resistance (or other electrical properties), the potentiometer resistor 340 is connected to a fixed resistor 330. The fixed resistor 330 is configured to maintain a predetermined resistance level, while the potentiometer resistor 340 is configured to adjust the resistance based on tension or stress applied to the element 305.

A measurement point 301 is employed to measure the voltage level on the fixed resistor 330. When the tension or stress changes, the voltage level at the measured point 301 is measured. The voltage level at this point changes as the difference in resistance between the fixed resistor 330 and the potentiometer resistor 340 changes. As an example, a user may place the apparatus 100 and/or 200 on his/her chest, and the measured voltage level can indicate the rise and fall of his/her chest, and subsequently the respiratory effort of the user.

In some embodiments, the tension of the element 305 is calibrated to have a baseline of the resistance and the measured voltage at the measurement point 301. The calibration can be performed, for example, during manufacture and/or during use. As a non-limiting example, the calibration may be determined based on the weight, age, sex, and other factors of a user. The calibration can be performed to ensure that the changes in the tension fall on the linear range of the potentiometer resistor 340. The measurement can be performed, e.g., by the processing circuitry 270 in the apparatus 200 shown in FIG. 2.

Figure 4A:
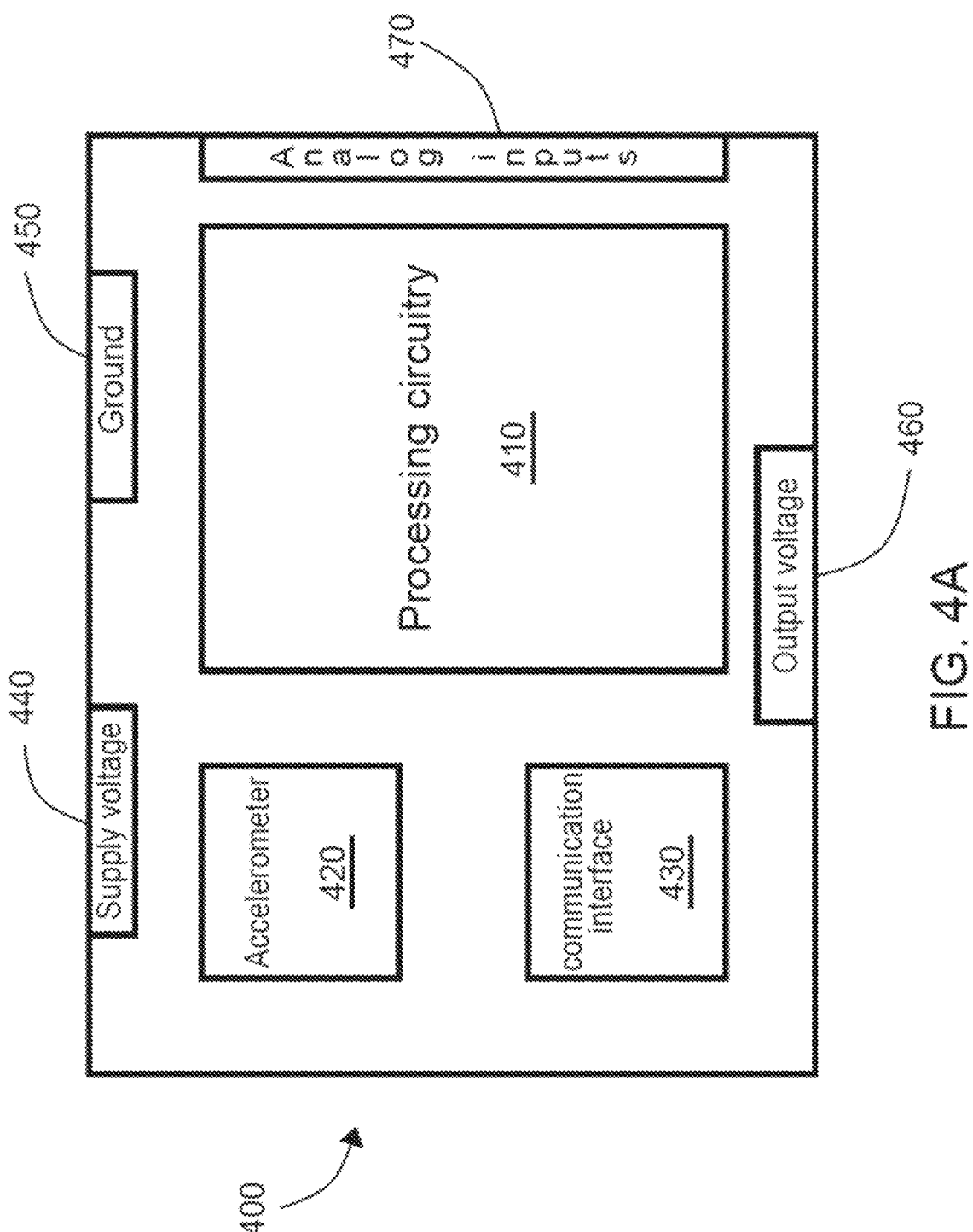
FIGS. 4A-4B show schematic illustrations of an apparatus having multiple functions to facilitate the monitoring of sleep parameters in accordance with some embodiments.
Figure 4B:
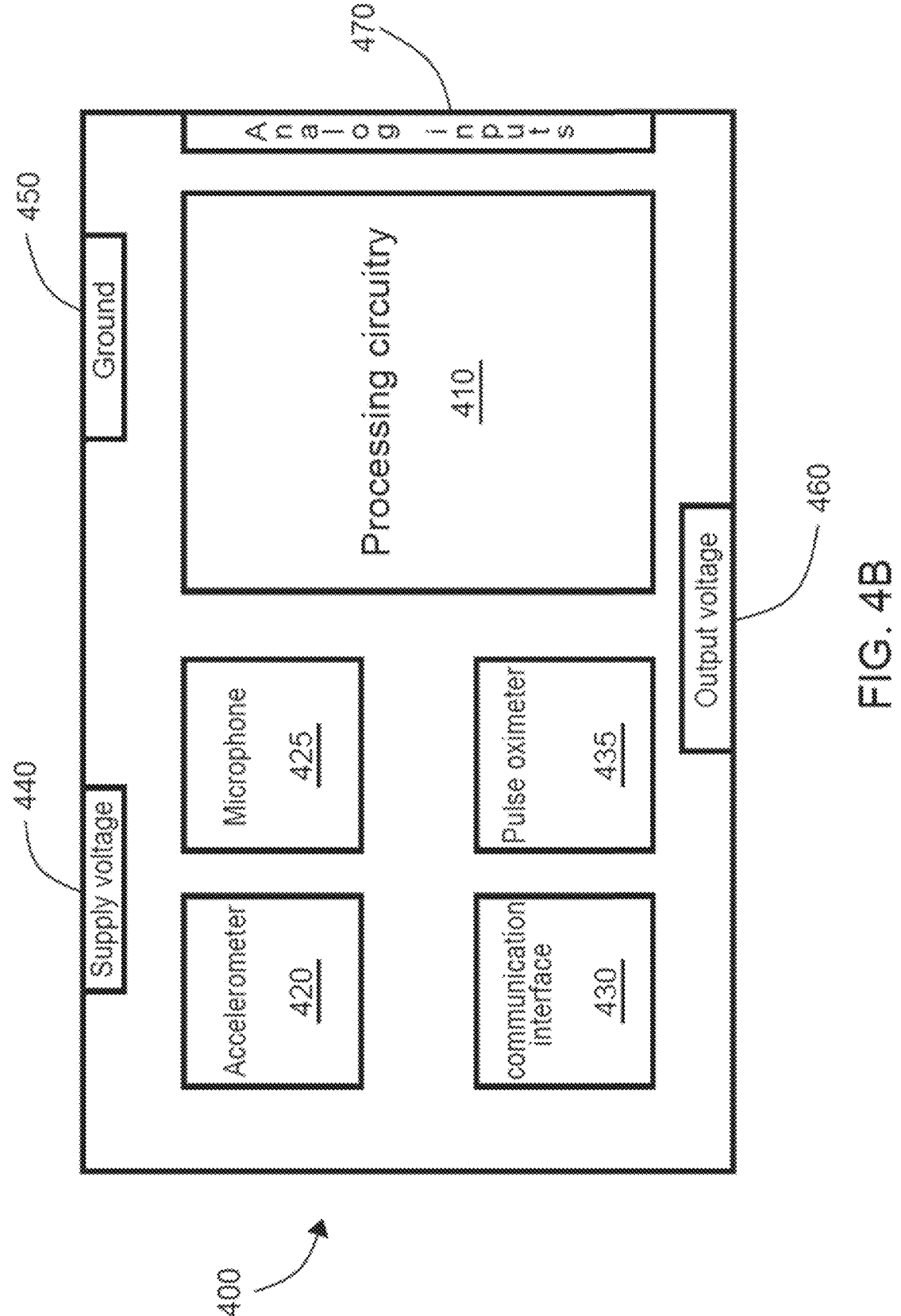

FIGS. 4A and 4B show schematic illustrations of an apparatus 400 having multiple functions to facilitate the monitoring of sleep parameters in accordance with some embodiments. The apparatus 400 shown in FIG. 4A includes a processing circuitry 410 operably coupled to an analog input 470 and a communication interface 430. A first port 440 (or interface) is employed to supply an input voltage to the apparatus 400, and a second port 450 (or interface) is connected to ground. The apparatus 400 also includes an output port 460 to deliver the output voltage.

The analog input 470 is operably coupled to one or more elements that are configured to generate measurable change in the electrical property in response to the breathing of the user. Signals (or data) representing such change is sent to the processing circuitry 410 for analysis via the analog input 470. In some embodiments, the analog input 470 can be replaced by a digital input, in which case an analog to digital converter (ADC) can be included before the digital input to digitize the signals generated by the elements.

The communication interface 430 can be substantially similar to the communication interface 240 shown in FIG. 2 and described above. The communication interface 430 is configured to connect the apparatus 400 to an external device (e.g., a personal computer, a smartphone, a smart watch, a tablet, etc.). The connection between the apparatus 400 and the external device can be bidirectional, i.e. the apparatus 400 can send data to the external device as well as receive data from the external device.

In some embodiments, the data from the apparatus 400 can be continuously sent to the external device for further processing or displaying. In some embodiments, the data from the apparatus 400 can be periodically sent to the external device at predetermined intervals. For example, the apparatus 400 can transmit the data at the end of every day. In another example, the apparatus 400 can transmit the data when the apparatus 400 is removed from the user (e.g., after use). In yet another example, the apparatus 400 can transmit the data when the apparatus 400 is attached to the user and stop transmitting the data when the apparatus 400 is removed from the user. In this example, the apparatus 400 can continuously transmit data to the external device during the use of the apparatus 400.

In some embodiments, the data from the apparatus 400 can be sent to the external device upon request. For example, the user can request the user's data via an application (or any other software program) installed on the external device. In another example, the user's doctor may also request the user's data using an external device. In some embodiments, the data in the apparatus 400 can be transmitted to a network server, and any interested party can have access to the data.

The apparatus 400 also includes an accelerometer 420 (or other motion sensor) operably coupled to the processing circuitry 410. Data acquired by the accelerometer 420 can be used to determine the respiratory effort, movements and sleep positions of the user (see, e.g., FIG. 21 and related discussion below). In some embodiments, this accelerometer data can be analyzed in combination with the data from the element so as to investigate the respiratory efforts of the user in different sleep positions and/or to improve signal/data quality. In some embodiments, the signal processing associated with respiratory effort can be based on the accelerometer data. Such investigation may help identify the possible sleep disorders of the user in certain particular positions.

The apparatus 400 shown in FIG. 4B includes two additional components: a microphone 425 and a pulse oximeter 435. The microphone 425 is configured to capture sound near or surrounding the apparatus 400. In some embodiments, the microphone 425 is configured to capture ambient noise near the apparatus 400. The ambient noise can include sound from the user's breathing and/or snoring. This microphone data can be used, for example, to analyze the sleep quality of the user. For example, the sound from the user's breathing can be used to analyze the breath rhythm of the user, which in turn can indicate the sleep quality. The sound from the snoring of the user can also reveal the sleep quality. For example, detection of excess snoring may be correlated with a high risk of sleep disorder.

In some embodiments, the ambient noise captured by the microphone 425 can also include sound from the heart, lungs, or other organs (e.g., wheezes, crackles, or lack thereof). In some embodiments, the processing circuitry 410 can be configured to identify and/or distinguish sounds from different sources so as to improve the accuracy of subsequent analysis. Such identification can be based on, for example, the rhythm and/or the spectrum (e.g., frequency) of the sound from each source.

The pulse oximeter 435 is configured to measure the oxygen saturation level (e.g., $SpO_2$) of the user. As used herein, the $SpO_2$ of a user refers to the percentage of oxygenated haemoglobin (i.e., haemoglobin that contains oxygen) compared to the total amount of haemoglobin (i.e., the total amount of oxygenated and non-oxygenated haemoglobin) in the blood of the user.

In some embodiments, the pulse oximeter 435 can measure the $SpO_2$ of the user via an optical method. In this optical method, the pulse oximeter 435 employs an emitter, such as a laser or a light emitting diode (LED) to emit a light beam (usually red or near infrared) to the skin of the user. A detector in the pulse oximeter 435 then detects light reflected, transmitted, or scattered from the user. The $SpO_2$ of the user can be derived from the absorption and/or reflection of the light beam. If the apparatus 400 detects that the $SpO_2$ of the user is below the normal range (e.g., below 95%), an alarm can be generated by the apparatus 400 to alert the user of possible issues with the user's lung functions.

FIG. 5A is a schematic illustration of an apparatus for monitoring a sleep parameter of a user, in accordance with some embodiments. The apparatus 500A includes a single adhesive pad 510 connected, at two places, to a series of three flexible elements 520a, 520b and 520c (collectively referred to as element 520). Each of the three flexible elements 520a, 520b and 520c can be of the same or differing composition, and can be one or more of: piezoresistive, conductive, or configured to exhibit a modified electrical property in response to an applied force or deformation. One or more of the three flexible elements 520a, 520b and 520c can include a fabric, such as a woven or nonwoven fabric. The adhesive pad 510 can be conformally attached to the surface of the user (e.g., on the skin, see FIGS. 6A-6C) and substantially secured to the surface of the user during use. When the user breathes (i.e., inhales and/or exhales), the area of the user's surface can change accordingly, thereby causing a change in a dimension (e.g., length and/or width) of one or more of the three flexible elements 520a, 520b and 520c. In other words, there can be an elongation or other deformation of one or more of the three flexible elements 520a, 520b and 520c, inducing corresponding change(s) in electrical properties of the one or more flexible elements 520a, 520b and 520c.

The apparatus 500A also includes a power source 530 electrically coupled to the flexible elements 520a, 520b and 520c, and one or more electrical circuits 540 (e.g., microelectronic chips) electrically coupled to the power source 530 and the flexible elements 520a, 520b and 520c. The electrical circuit(s) 540 are configured to detect, during use, the change of an electrical property of one or more of the flexible elements 520a, 520b and 520c (e.g., individually or in aggregate). In some embodiments, the electrical circuits 540 can further include a processor (see, e.g., FIG. 2) to process the data representing the change of the electrical property of the one or more of the flexible elements 520a, 520b and 520c, so as to calculate the sleep parameter of the user (or any other respiratory or biomechanical parameter).

In some embodiments, an apparatus (such as apparatus 500A of FIG. 5A) includes three flexible elements, each of which is configured to exhibit a modified electrical property (e.g., resistance, resistivity, reactance, impedance, etc.) in response to an applied force (e.g., pressure, compression, tension, etc.). When all three flexible elements are configured to exhibit a modified electrical property in response to an applied force, the apparatus can be used to detect a volume change associated with the user/wearer. In other embodiments, an apparatus (such as apparatus 500 of FIG. 5A) includes three flexible elements, only one of which is configured to exhibit a modified electrical property (e.g., resistance, resistivity, reactance, impedance, etc.) in response to an applied force (e.g., pressure, compression, tension, etc.). When only one of the three flexible elements is configured to exhibit a modified electrical property in response to an applied force, the apparatus can be used to detect a unidirectional dimensional change associated with the user/wearer. Although the series of three flexible elements 520a, 520b and 520c is shown in FIG. 5A as extending, in two places, from adhesive pad 510, in other embodiments any one, any two, or all three of the three flexible elements 520a, 520b and 520c can be disposed on the adhesive pad 510 itself.

Figure 5B:
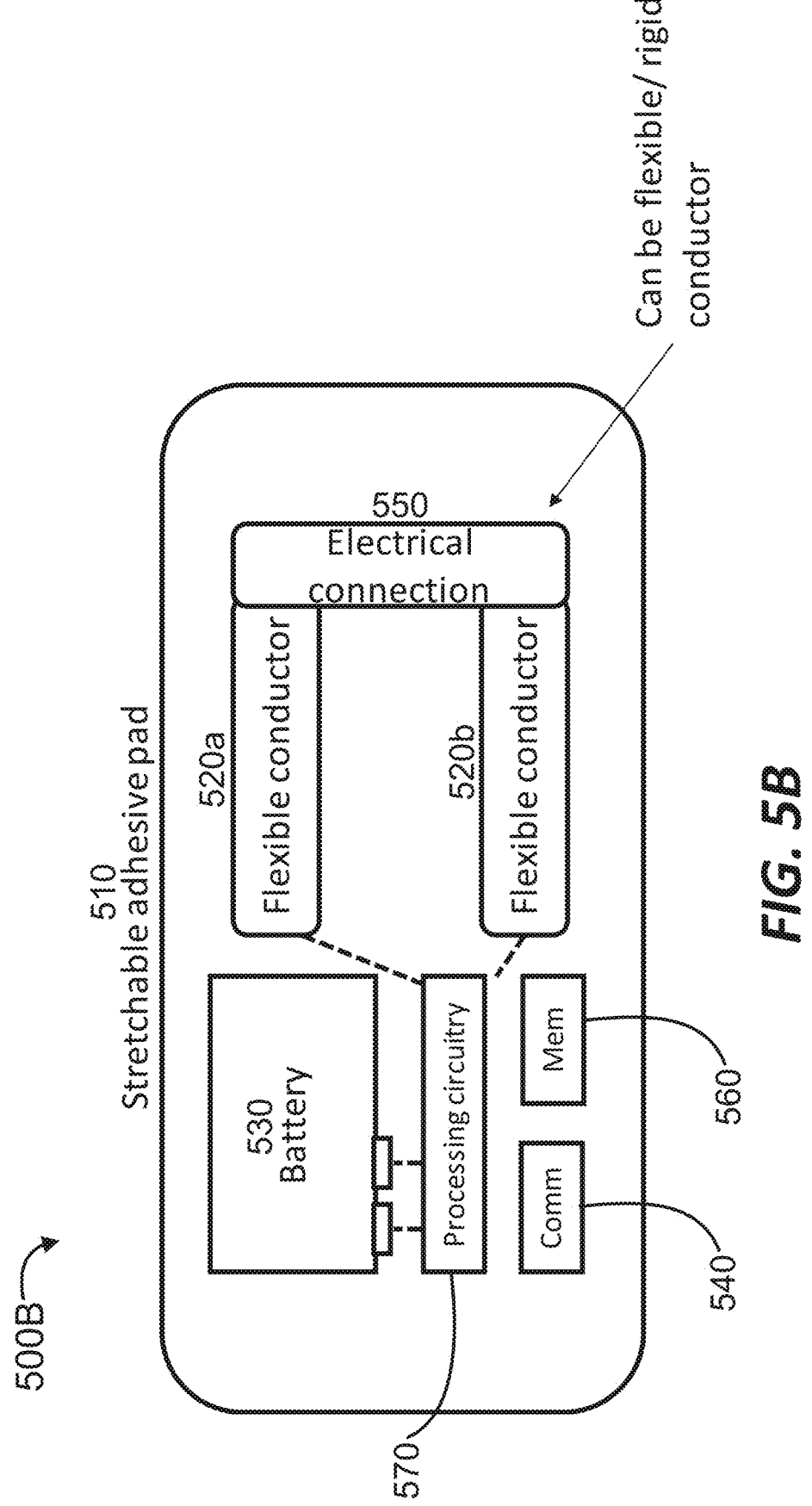
FIG. 5B is a schematic illustration of an apparatus for monitoring a sleep parameter of a user, in accordance with some embodiments.

FIG. 5B is a schematic illustration of an apparatus for monitoring a sleep parameter of a user, in accordance with some embodiments. The apparatus 500B includes a single, stretchable adhesive pad 510 upon which are arranged two flexible conductor elements 520a and 520b, electrically connected to one another by an electrical connection 550. The electrical connection 550 can be flexible or rigid. Each of the flexible conductor elements 520a, 520b can be of the same or differing composition, and can be one or more of:

piezoresistive, conductive, or configured to exhibit a modified electrical property in response to an applied force or deformation. One or more of the two flexible conductor elements 520*a* and 520*b* can include a fabric, such as a woven or nonwoven fabric, and/or a conductive polymer material. The adhesive pad 510 can be conformally attached, during use, to the surface of the user (e.g., on the skin, see FIGS. 6A-6C) and substantially secured to the surface of the user during use. When the user breathes (i.e., inhales and/or exhales), the area of the user's surface can change accordingly, thereby causing a change in a dimension (e.g., length and/or width) of one or more of the two flexible conductor elements 520*a* and 520*b*. In other words, there can be an elongation or other deformation of one or more of the two flexible conductor elements 520*a* and 520*b*, inducing corresponding change(s) in electrical properties of one or both of the two flexible conductor elements 520*a* and 520*b*.

Figure 5D:
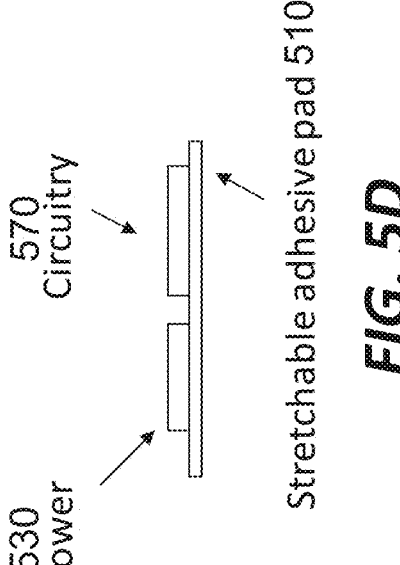
FIGS. 5C-D are side and back view illustrations, respectively, of the apparatus of FIG. 5B.
Figure 5C:
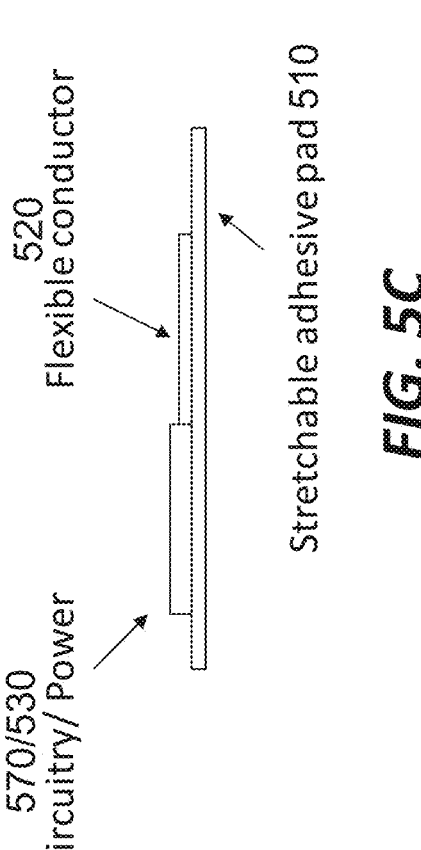

The apparatus 500B also includes a battery 530 electrically coupled to processing circuitry 570, which in turn is electrically coupled to the flexible conductor elements 520*a*, 520*b*. Onboard communications component 540 and processing circuitry 570 can be electrically coupled to the battery 530 and/or the flexible conductor elements 520*a*, 520*b*. The processing circuitry 570 can be configured to detect, during use, the change of an electrical property of one or both of the flexible conductor elements 520*a*, 520*b* (e.g., individually/separately or in aggregate). In some embodiments, the processing circuitry 570 can further include a processor (see, e.g., FIG. 2) to process the data representing the change of the electrical property of the one or more of the flexible conductor elements 520*a* and 520*b*, so as to calculate the sleep parameter of the user (or any other respiratory or biomechanical parameter). FIGS. 5C-D are side and back view illustrations, respectively, of the apparatus 500B of FIG. 5B.

Figure 5E:
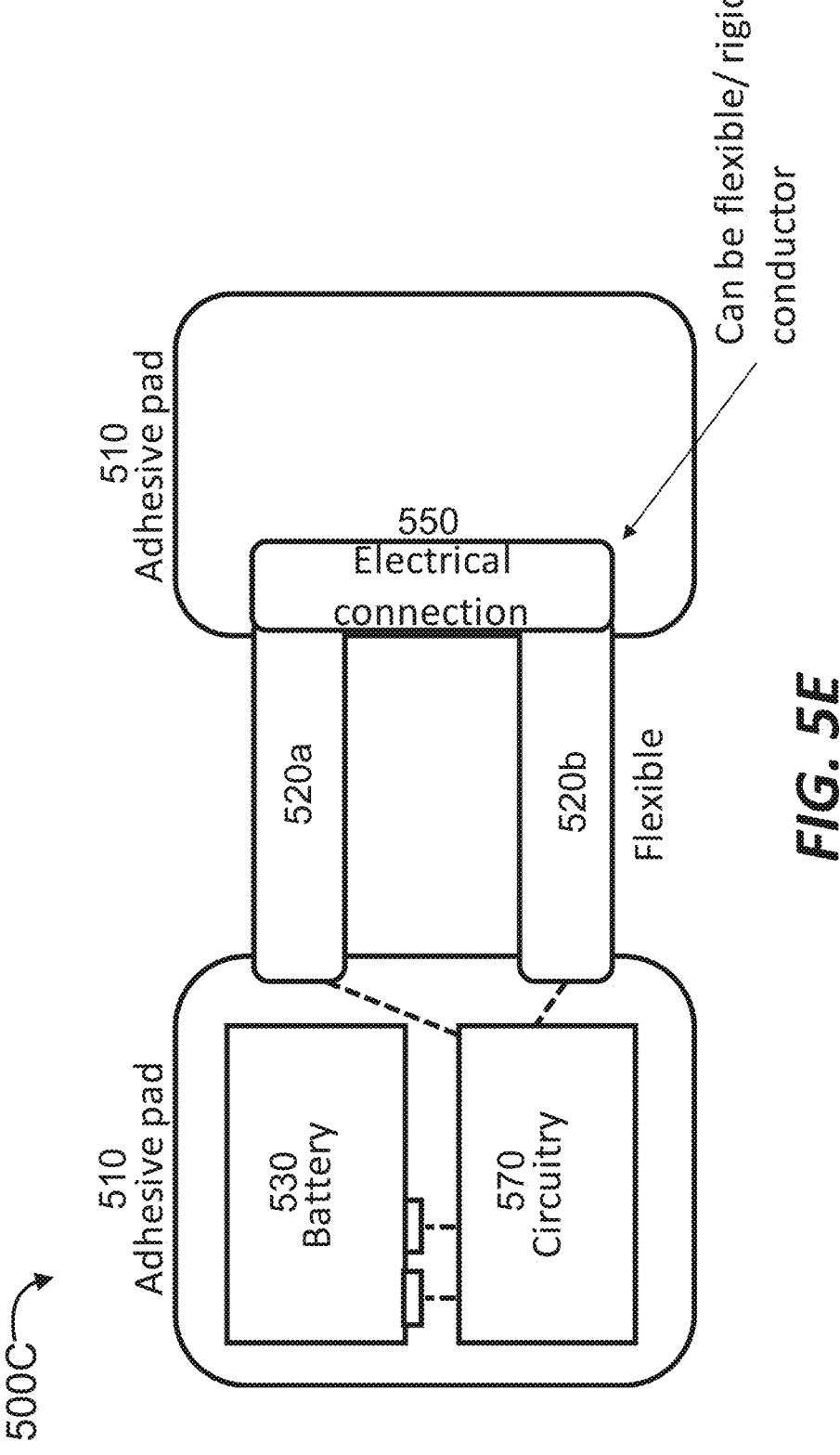
FIG. 5E is a schematic illustration of an apparatus for monitoring a sleep parameter of a user, in accordance with some embodiments.

FIG. 5E is a schematic illustration of an apparatus for monitoring a sleep parameter of a user, in accordance with some embodiments.

The apparatus 500C includes two adhesive pads 510 connected to one another by two flexible conductor elements 520*a* and 520*b*, electrically connected to one another by an electrical connection 550 disposed at least partially on one of the two adhesive pads. The electrical connection 550 can be flexible or rigid. Each of the flexible conductor elements 520*a*, 520*b* can be of the same or differing composition, and can be one or more of: piezoresistive, conductive, or configured to exhibit a modified electrical property in response to an applied force or deformation. One or more of the two flexible conductor elements 520*a* and 520*b* can include a fabric, such as a woven or nonwoven fabric, and/or a conductive polymer material. The adhesive pads 510 can be conformally attached, during use, to the surface of the user (e.g., on the skin, see FIGS. 6A-6C) and substantially secured to the surface of the user during use. When the user breathes (i.e., inhales and/or exhales), the area of the user's surface can change accordingly, thereby causing a change in a dimension (e.g., length and/or width) of one or more of the two flexible conductor elements 520*a* and 520*b*. In other words, there can be an elongation or other deformation of one or more of the two flexible conductor elements 520*a* and 520*b*, inducing corresponding change(s) in electrical properties of one or both of the two flexible conductor elements 520*a* and 520*b*.

Figure 5G:
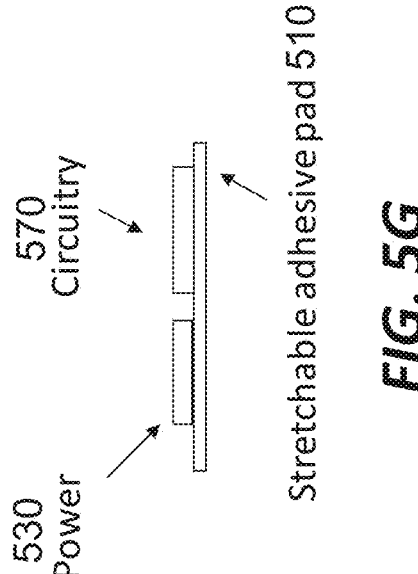
FIGS. 5F-G are side and back view illustrations, respectively, of the apparatus of FIG. 5E.
Figure 5F:
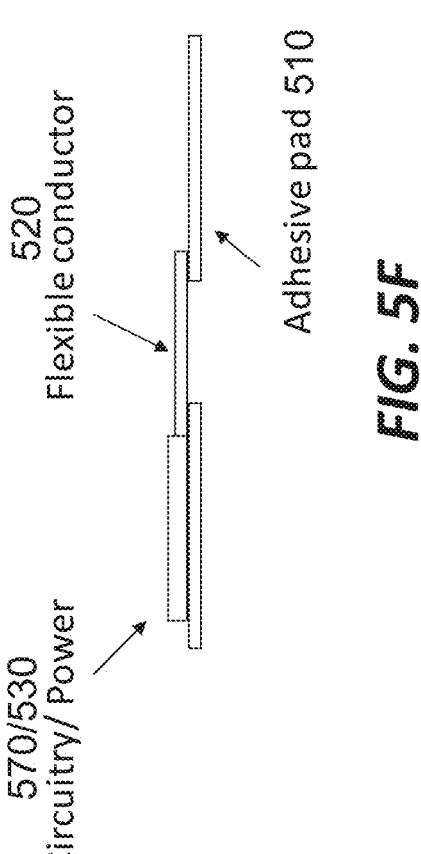

The apparatus 500C also includes a battery 530 electrically coupled to circuitry 570, which in turn is electrically coupled to the flexible conductor elements 520*a*, 520*b*. The circuitry 570 can be electrically coupled to the battery 530 and/or the flexible conductor elements 520*a*, 520*b*. The processing circuitry 570 can includes one or more processors, one or more communications modules, and/or a memory operably coupled to the one or more processors and storing processor-executable instructions. The circuitry 570 can be configured to detect, during use, the change of an electrical property of one or both of the flexible conductor elements 520*a*, 520*b* (e.g., individually/separately or in aggregate). In some embodiments, a processor of the processing circuitry 570 is configured to process the data representing the change of the electrical property of the one or more of the flexible conductor elements 520*a* and 520*b*, so as to calculate the sleep parameter of the user (or any other respiratory or biomechanical parameter). FIGS. 5F-G are side and back view illustrations, respectively, of the apparatus 500C of FIG. 5E.

Figure 5H:
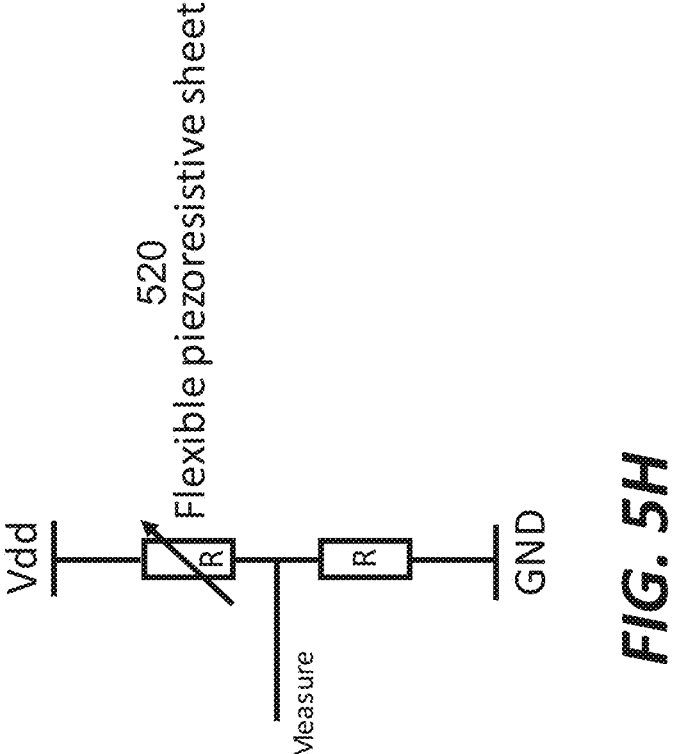
FIG. 5H is a schematic of a circuit for measuring respiratory effort using a flexible piezoresistive sheet, in accordance with some embodiments.

FIG. 5H is a schematic of a circuit for measuring respiratory effort using a flexible piezoresistive sheet, in accordance with some embodiments. The circuit of FIG. 5H can be incorporated into any conductor element of any embodiment set forth herein.

Figure 5I:
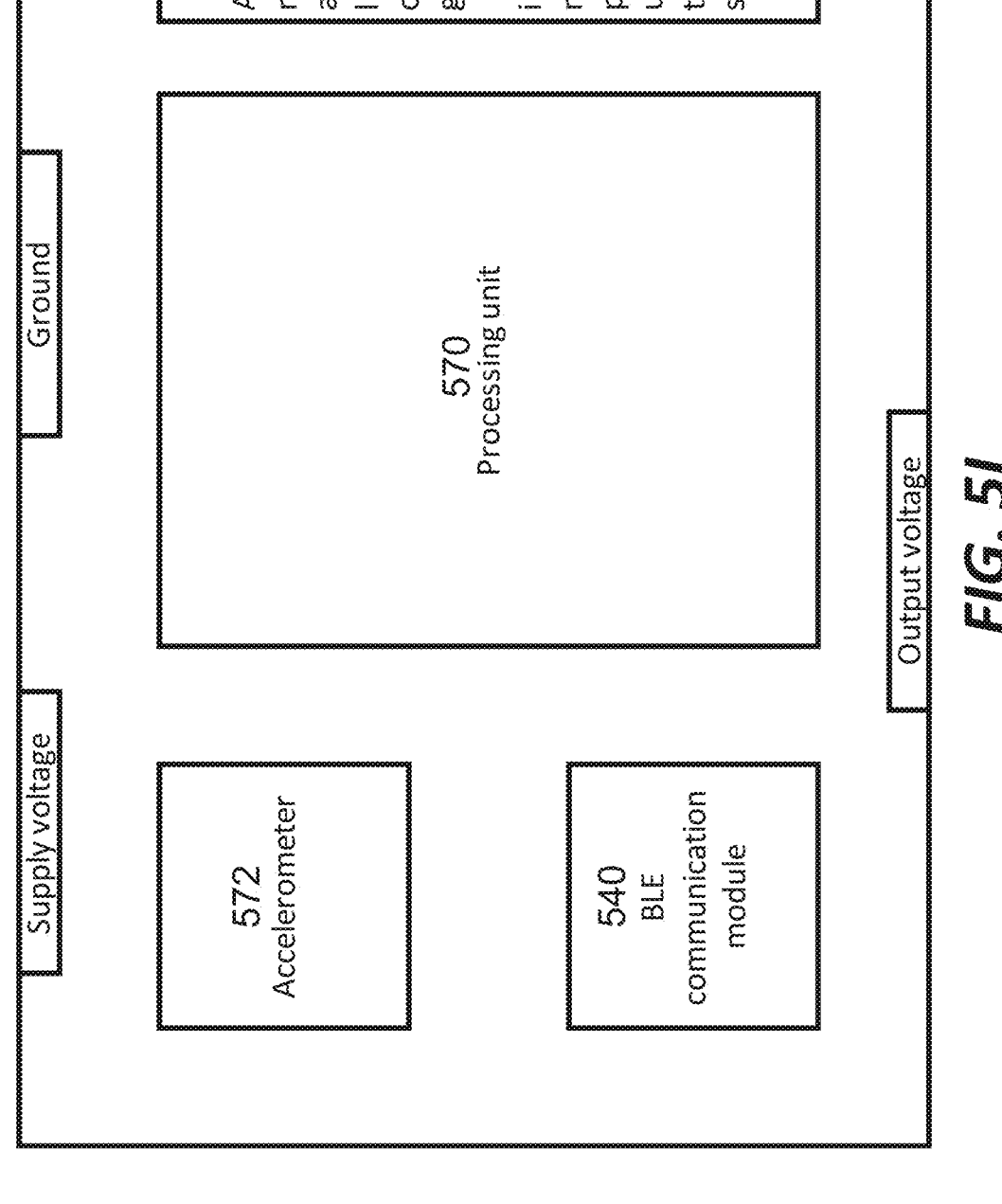
FIGS. 5I-5J show schematic illustrations of a processing and communications unit, in accordance with some embodiments.
Figure 5J:
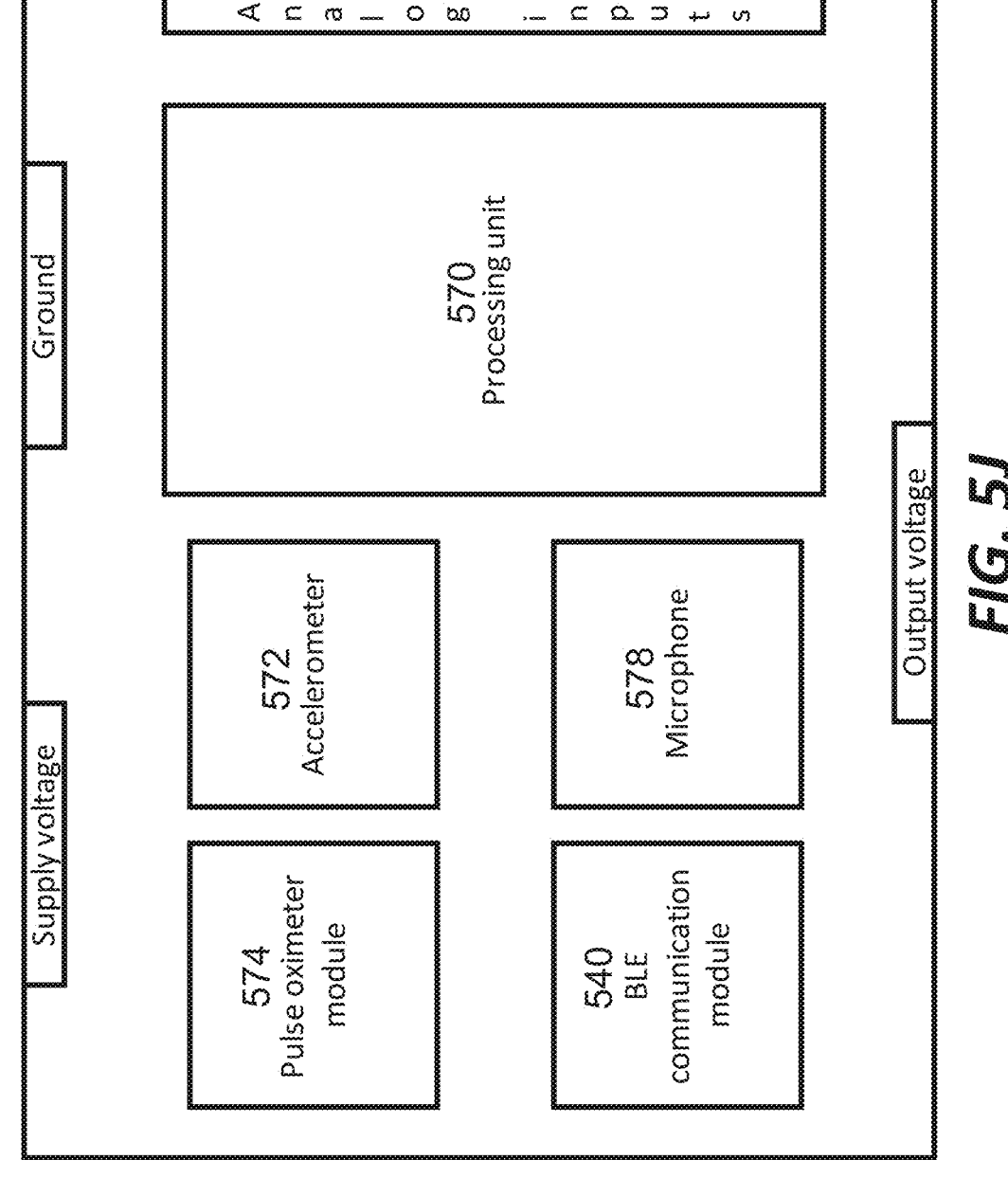

FIGS. 5I-5J show schematic illustrations of a processing and communications unit, compatible with apparatuses described herein, in accordance with some embodiments. As shown in FIG. SI, a processing and communications unit 502 has one or more analog inputs, and electrical terminals for supply voltage, output voltage, and ground. The processing and communications unit 502 includes an accelerometer 572, a BLE communication module 540, and a processing unit 570. In FIG. 5J, a processing and communications unit 504 has one or more analog inputs, and electrical terminals for supply voltage, output voltage, and ground. The processing and communications unit 504 includes an accelerometer 572, a BLE communication module 540, a pulse oximeter module 574, a microphone 5778, and a processing unit 570.

In some embodiments, a system for monitoring a sleep parameter of a user includes a portable electronic device, a first patch sensor, and a second patch sensor. The first patch sensor includes a first adhesive pad configured to conform to a first surface of the user, a first flexible conductive strip coupled to the first adhesive pad, and a first electrical circuit electrically coupled to the first flexible conductive strip. The first flexible conductive strip is configured to exhibit a modified electrical property in response to an applied force. The first electrical circuit is configured to detect, during use, a change in an electrical property of the first flexible conductive strip. The second patch sensor includes a second adhesive pad configured to conform to a second surface of the user different from the first surface of the user, a second flexible conductive strip coupled to the second adhesive pad, and a second electrical circuit electrically coupled to the second flexible conductive strip. The second flexible conductive strip is configured to exhibit a modified electrical property in response to an applied force. The second electrical circuit is configured to detect, during use, a change in an electrical property of the second flexible conductive strip. Each of the first electrical circuit and the second electrical circuit is configured to transmit electrical property change data to the portable electronic device for determination of the sleep parameter.

In some embodiments, a system for monitoring a sleep parameter of a user includes a portable electronic device, a first patch, and a second patch, where only first patch includes a flexible conductive strip/sensing element, and the second patch does not include a flexible conductive strip/sensing element. The first patch sensor includes a first adhesive pad configured to conform to a first surface of the user, the flexible conductive strip coupled to the first adhesive pad, and a first electrical circuit electrically coupled to the first flexible conductive strip. The flexible conductive strip is configured to exhibit a modified electrical property in response to an applied force. The first electrical circuit is configured to detect, during use, a change in an electrical property of the first flexible conductive strip. In some such implementations, the second patch sensor includes a second adhesive pad configured to conform to a second surface of the user different from the first surface of the user, and one or more of: an accelerometer, a power source, a processor, a communications module, a pulse oximeter, or a second electrical circuit. The second patch can be configured, for example, to measure/track limb movements for PLMD and/or RLS (e.g., based on an onboard accelerometer), other body positioning, and/or oxygen levels/saturation and heart rate (e.g., based on an onboard pulse oximeter) from disparate locations on the wearer's body. Acquisition of signals from different body parts of a wearer can result in improved signal quality (e.g., higher signal-to-noise ratio (SNR)) and/or improved data accuracy. The system can be configured such that data from one or both of the first patch and the second patch can be transmitted to and/or synchronized with a mobile device (such as a smartphone). One or both of the first electrical circuit and the second electrical circuit can be configured to transmit electrical property change data to a portable electronic device for determination of the sleep parameter.

In some embodiments, a system for monitoring a sleep parameter of a user includes a portable electronic device, a first patch, and a second patch, where neither the first patch nor the second patch includes a flexible conductive strip/sensing element. Each of the first patch and the second patch can include an adhesive pad configured to conform to a second surface of the user different from the first surface of the user, and one or more of: an accelerometer, a power source, a processor, a communications module, a pulse oximeter, or a second electrical circuit. The first and second patch, whether individually or in combination, can be configured, for example, to measure/track limb movements for PLMD and/or RLS (e.g., based on an onboard accelerometer), other body positioning, and/or oxygen levels/saturation and heart rate (e.g., based on an onboard pulse oximeter) from disparate locations on the wearer's body. Data collected by the first and second patches can be transmitted, e.g., via wired or wireless communication, to a compute device of a physician or technician, for sleep disorder examination.

Figure 6A:
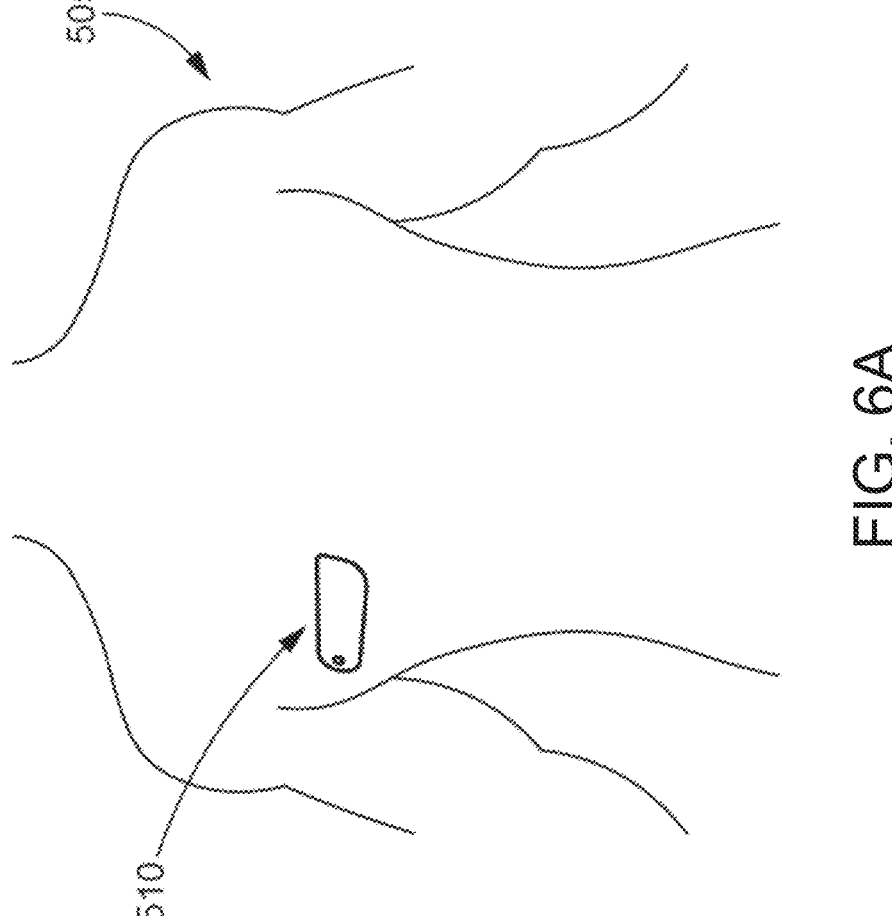
FIG. 6A illustrates a location on a user to place an apparatus for monitoring the respiratory effort of the user, in accordance with some embodiments.
Figure 6B:
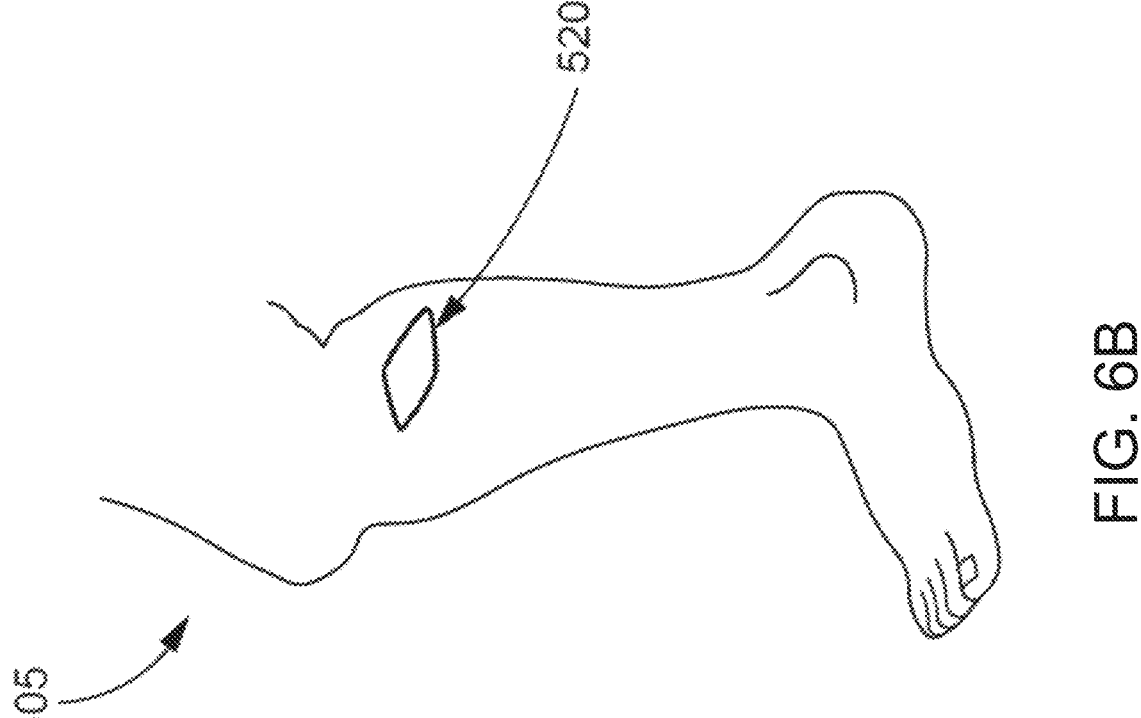
FIG. 6B illustrates a location on a user to place an apparatus for monitoring limb movement of the user, in accordance with some embodiments.
Figure 6C:
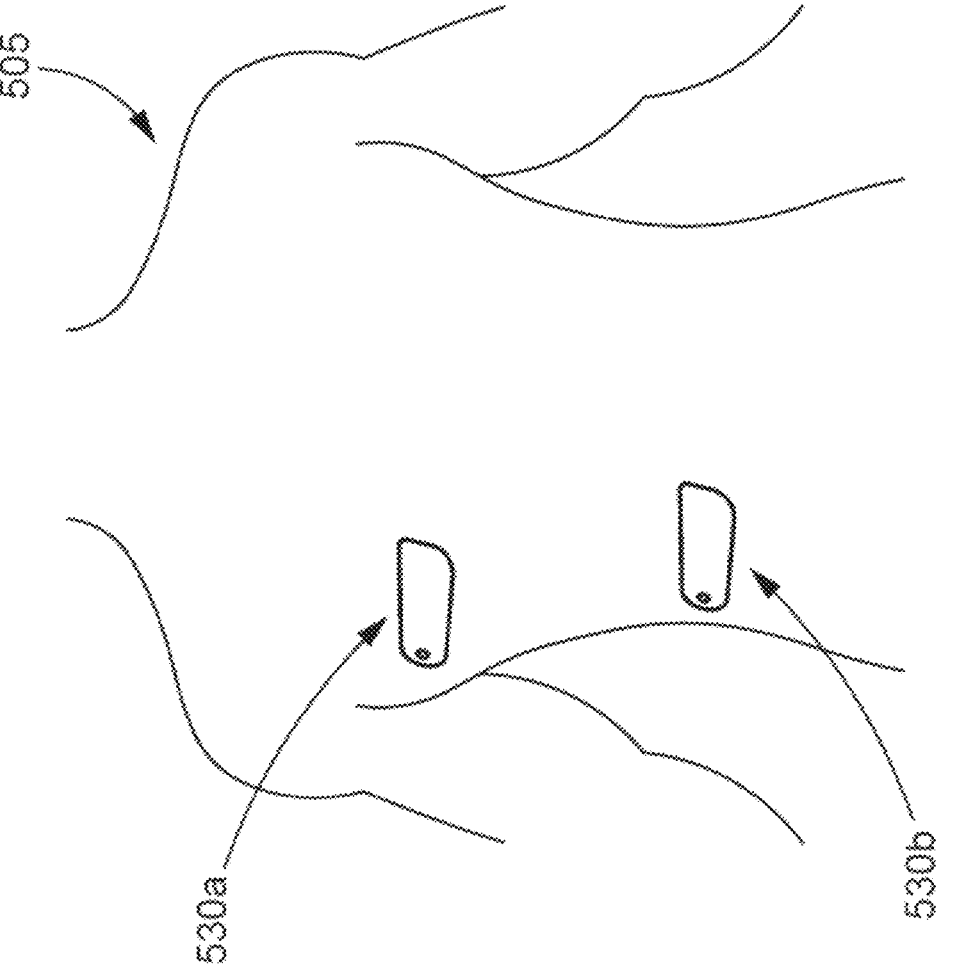
FIG. 6C illustrates a location on a user to place an apparatus for monitoring the respiratory effort of the user, in accordance with some embodiments.

FIGS. 6A-6C illustrate different locations on a user to place an apparatus for monitoring the respiratory effort of the user in accordance with some embodiments. FIG. 6A shows that an apparatus 510 can be placed on the chest of a user 505. FIG. 6B shows that an apparatus 520 can be placed on a limb (e.g., leg) of the user 505 to monitor limb movement, for example to assess parameters associated with periodic limb movement disorder (PLMD), restless limb syndrome (RLS). The apparatuses 510 and 520 can be substantially similar to any of the apparatus described herein (e.g., 100 in FIG. 1A, 200 in FIG. 2, and 400 in FIGS. 4A and 4B). In addition, the apparatuses 510 and 520 are configured as patches that can be conformally attached to the body of the user 505 and can be worn by the user for an extended period of time (e.g., overnight) without causing excess discomfort to the user 505.

FIG. 6C shows that two apparatuses 530a and 530b (also referred to as sensors 530a and 530b) are placed on the user 505. The first sensor 530a is placed on a first location (e.g., chest) of the user 505 and the second sensor 530b is placed on a second location (e.g., abdomen), different from the first location, of the user 505. This configuration of using two sensors 530a and 530b configured as patches can be employed to measure a respiratory airflow of the user 505. For example, sensor data from sensors 530a and 530b can be one or more of: summed, input to a machine learning algorithm, or combined with other physical parameters. In some embodiments, the determination of an airflow of a patient is based on sound (i.e., audio signals) emitted from the patient's lungs and/or airways. Conventionally, the airflow estimation is conducted using facial appliances, such as a nasal cannula or a thermistor. In contrast, the measurement of airflow described herein is based on the respiratory effort signals provided by the sensors 530a and 530b including at least one piezoresistive element. The use of adhesive patches set forth herein improves the accuracy of the airflow estimation, as the sensors 530a and 530b can maintain their positions during the entire measurement period.

In some embodiments, the two sensors 530a and 530b can be substantially similar to any of the apparatus described herein (e.g., 100 in FIG. 1A, 200 in FIG. 2, and 400 in FIGS. 4A and 4B). In some embodiments, the two sensors 530a and 530b are substantially identical to each other.

In some embodiments, the two sensors 530a and 530b can be different from each other. For example, one sensor (e.g., 530a) can include an accelerometer and does not include an oximeter, and the other sensor (e.g., 530b) can include a pulse oximeter and does not include an accelerometer. In this instance, the two sensors 530a and 530b can supplement each other. In another example, one sensor (e.g., 530a) can have multiple functions (e.g., similar to the apparatus 400 shown in FIG. 4B), such as accelerometer and pulse oximeter, while the other sensor (e.g., 530b) can include a more basic model (e.g., without accelerometer and pulse oximeter). In another example, one sensor (e.g., 530a) can include a piezoresistive element, and the other sensor (e.g., 530b) can include an element that is conductive but that does not exhibit piezoresistive behavior.

FIG. 6C illustrates two sensors 530a and 530b for monitoring respiratory efforts of the user 505. In some embodiments, multiple patches (e.g., more than two sensors) can be placed in a modular fashion at different locations on the user 505. Accordingly, the multiple patches operate simultaneously to facilitate complex measurements that assess sleep disorders, such as periodic limb movement disorder (PLMD), restless limb syndrome (RLS), and the like.

FIG. 7 is a flowchart illustrating a method 600 of monitoring the respiratory effort of a user, in accordance with some embodiments. The method 600 includes, at 610, adhering an apparatus to the skin of the user. In some embodiments, the apparatus can be substantially similar to any of the apparatus described herein (e.g., 100 in FIG. 1A, 200 in FIG. 2, and 400 in FIGS. 4A and 4B). For example, the apparatus can include a conductive element, such as a piezoresistive element made of a conductive, nonwoven fabric. The method also includes, at 620, applying an electric current to the conductive element. The electrical property (e.g., resistance, reactance, impedance, conductance, etc.) of the conductive element can also be recorded at this moment (also referred to as the initial value of the electrical property).

The apparatus is configured to measure, at 630, a change in the electrical property of the conductive element when the apparatus is adhered to the skin of the user. Such a change in the electrical property can be induced, for example, by the breathing of the user (e.g., inhalation and/or exhalation). In some embodiments, the apparatus also includes an adhesive pad configured to conform to a surface of the user (e.g., skin of the user). A power source is employed to power the conductive element, and an electrical circuit is electrically coupled to the power source as well as to the conductive element to detect, during use, the change in electrical property of the conductive element.

At 640, a distortion of the conductive element is calculated based on the measured change in the electrical property of the conductive element. In some embodiments, the distortion can be calculated by a processor included in the apparatus. In some embodiments, the apparatus can be configured to transmit (e.g., via a wired communication channel or a wireless communication channel) the raw data representing the change in the electrical property of the conductive element to an external device (e.g., a computer, a smartphone, a tablet, a network server, etc.). The external device can then calculate the distortion of the conductive element. At 650, the respiratory effort of the user is determined based on the distortion of the conductive element.

In some embodiments, the more than one apparatus can be used to monitor the respiratory effort of the user. For example, the apparatus described above can be a first apparatus and the distortion of the piezoresistive element is a first distortion of the piezoresistive element. The method further includes adhering a second apparatus to the skin of a user and calculating, based on a measured change in electrical property of a piezoresistive element of the second apparatus, a second distortion of the piezoresistive element of the second apparatus. The first distortion of the first piezoresistive element and the second distortion of the second piezoresistive element can be analyzed together to determine, for example, one or more of: the respiratory effort of the user, an airflow of the user, or a paradoxical breathing of the user (associated with a breathing obstruction).

In some embodiments, the first apparatus can be configured to measure the distortion of the first piezoresistive element along a first direction, and the second apparatus can be configured to measure the distortion of the second piezoresistive element along a second direction different from the first direction. In some embodiments, the first direction can be substantially perpendicular to the second direction.

In some embodiments, a third apparatus (e.g., similar to the first and second apparatus) can also be employed to facilitate the monitoring of the respiratory effort. For example, the third apparatus can be employed to measure the distortion of a third piezoresistive element along a third direction different from the first direction and the second direction. Such three-dimensional (3D) measurement can increase the accuracy in estimating the respiratory effort.

In some embodiments, data acquired by the apparatus in the method 700 is employed to determine the respiratory airflow of the user. In some embodiments, one or more sleep parameters (e.g., respiratory flow) and/or other biomechanical parameters can be identified or estimated based on the respiratory effort. In some embodiments, the measured/monitored parameters can include and/or can be associated with at least one of insomnia, sleep apnea, PLMD, and RLS. In some embodiments, data collected by apparatuses described herein can be supplemented by signals detected by a nasal cannula or thermistor.

Figure 8:
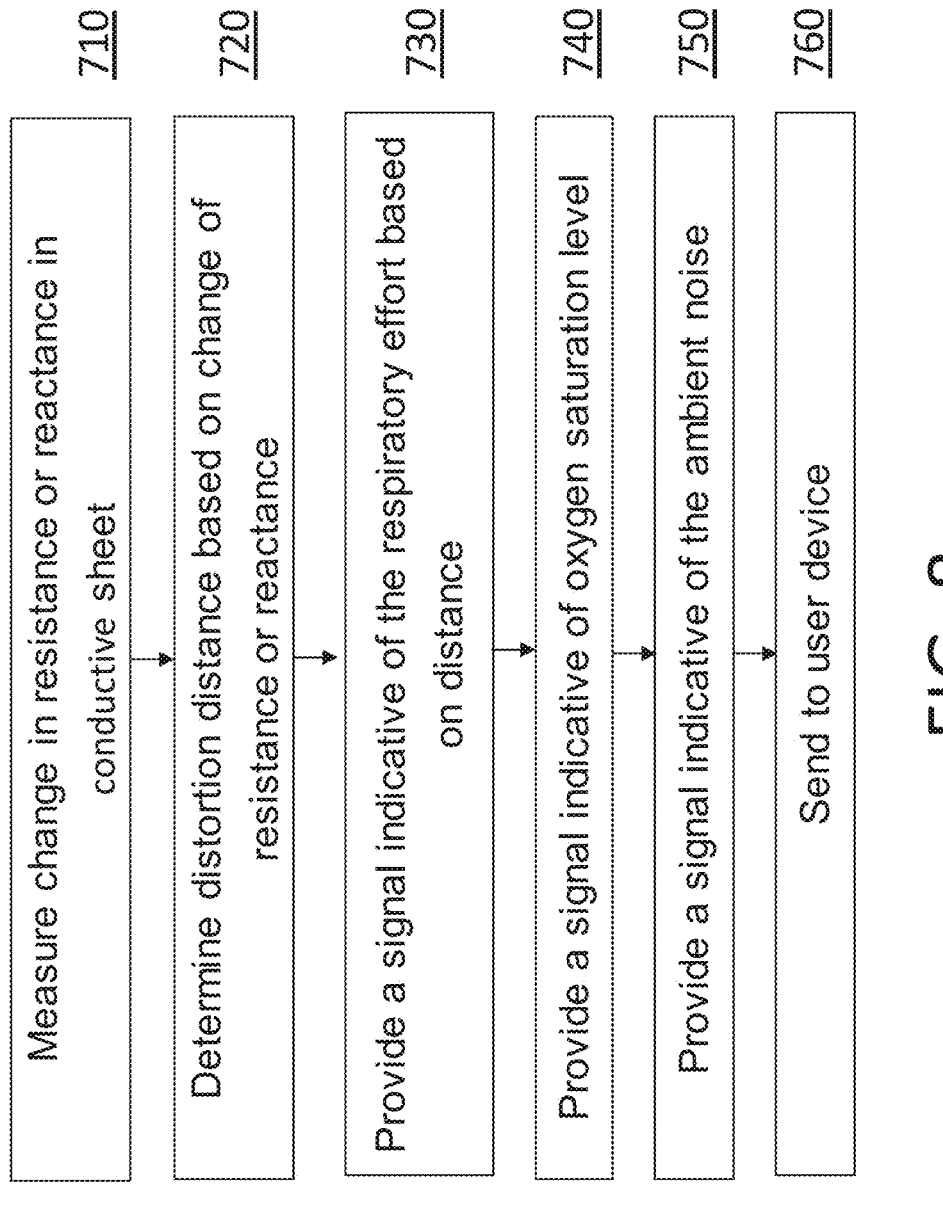
FIG. 8 is a flowchart illustrating a method of monitoring sleep parameters of a user in accordance with some embodiments.

FIG. 8 is a flowchart illustrating a method 700 of monitoring sleep parameters in accordance with some embodiments. At 710, a change in resistance and/or reactance is measured from a conductive material, such as the piezoresistive element described herein (e.g., 120 in FIG. 1A and 220 in FIG. 2). The change in the resistance and/or reactance can be measured by an electrical circuit similar to the circuit 140 described herein with reference to FIG. 1A.

In some embodiments, the change in resistance and/or reactance is linearly related to the stress or tension applied to the conductive (optionally piezoresistive) material, i.e., linear regime. In some embodiments, the change in resistance and/or reactance can be a nonlinear function of the stress or tension applied to the conductive material. In either instance, a calibration step can be performed to establish a correlation between the applied tension/stress and the change of resistance and/or reactance of the conductive material.

At 720, the distance by which the conductive material has been distorted from a starting position is determined based on the change in resistance and/or reactance. This distance is also referred to the distortion of the conductive material. In some embodiments, the distortion is induced by the breathing of the user (e.g., inhalation and/or exhalation).

The method 700 also includes, at 730, generating a signal indicative of a breathing rate and respiratory effort of the user based on the determined distortion over a period of time. In some embodiment, the period of time can be overnight. In some embodiments, the period of time can be about 5 minutes to about 8 hours (e.g., about 5 minutes, about 10 minutes, about 20 minutes, about 30 minutes, about 1 hour, about 2 hours, about 3 hours, about 4 hours, or about 8 hours, including any values and sub ranges in between).

In some embodiments, the method 800 can also include one or more optional steps, such as generating a signal indicative of the oxygen saturation level of the user (at 740), and/or generating a signal indicative of ambient noise in the room environment when the user sleeps is recorded (at 750). The signal indicative of the oxygen saturation level of the user may be used to estimate the breathing efficiency of the user. Without being bound by any particular theory or mode of operation, breathing efficiency as used herein refers to the efficiency of delivering oxygen into blood from each breath.

In some embodiments, the signal indicative of the ambient noise can be further decomposed into several signals, each of which is contributed by a distinct sound source. Possible sound sources include breath of the user, snoring of the user, heartbeat of the user, appliances in the room (e.g., refrigerator, television, etc.), and street noise, among others.

In some embodiments, the method 700 can also include recording the movement of the user during sleep, including the sleep position or movements related to sleep disorders (such as PLMD or insomnia). All specified parameters may be indicative of potential sleep issues related to the user.

At 760, the data collected, including the signal indicative of respiratory effort, the signal indicative of oxygen saturation level, and the recorded ambient noise levels, are sent to a user device, e.g., to a smartphone over a wireless connection. In some embodiments, the user device can be configured to perform additional processing, such as visualization. In some embodiments, the user device can be configured to display the measurements.

In some embodiments, the data can be transmitted to a network server. The user can access the data using a user device such as a smartphone. In addition, a doctor may also gain access to the data so as to examine the sleep quality of the user. In some embodiments, the data contributed by multiple users can be used to conduct research related to sleep disorder treatments using, for example, big data analysis.

Figure 9A:
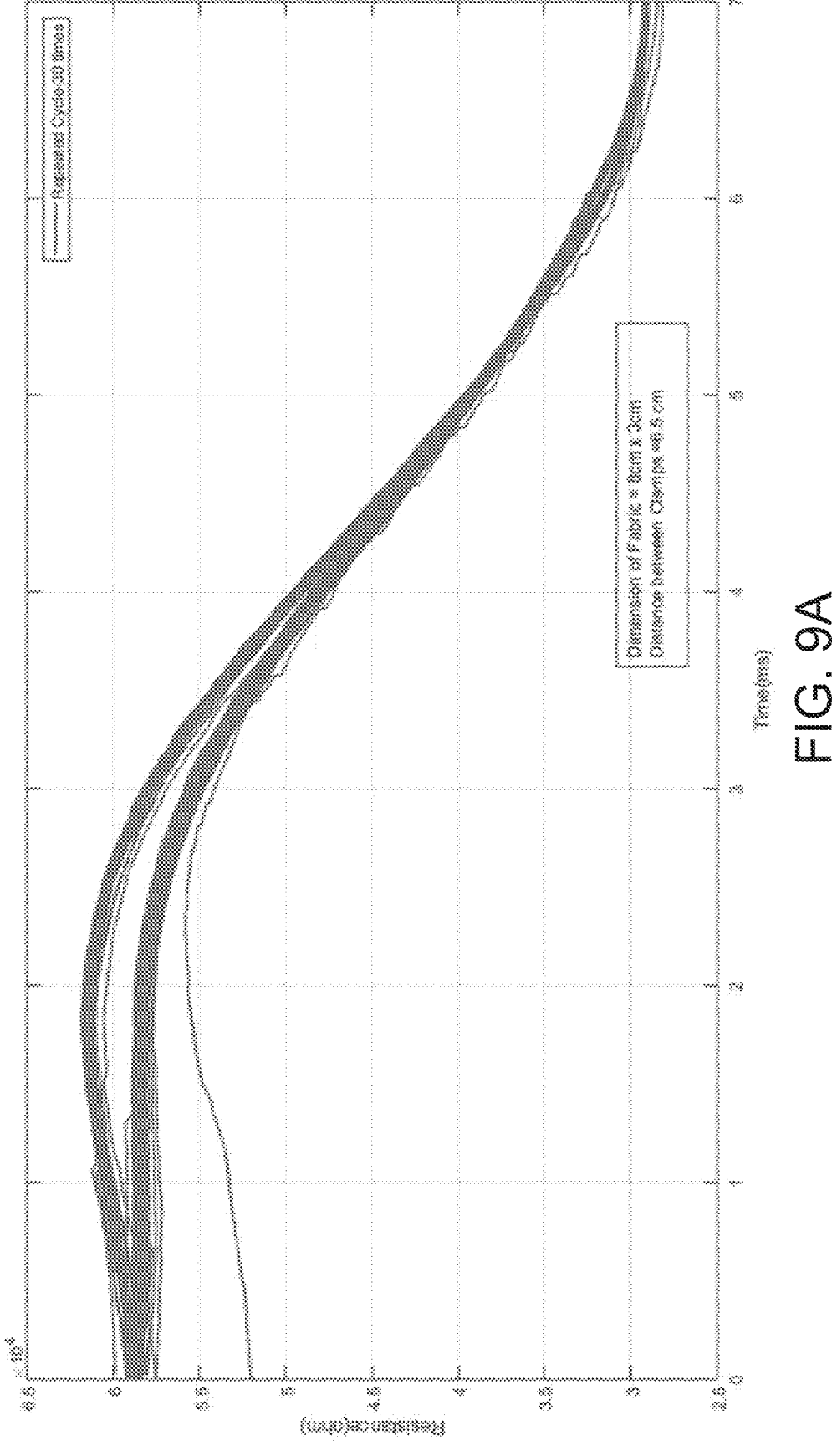
FIGS. 9A-9B show measured resistance change over time during length changes of elements in accordance with some embodiments.
Figure 9B:
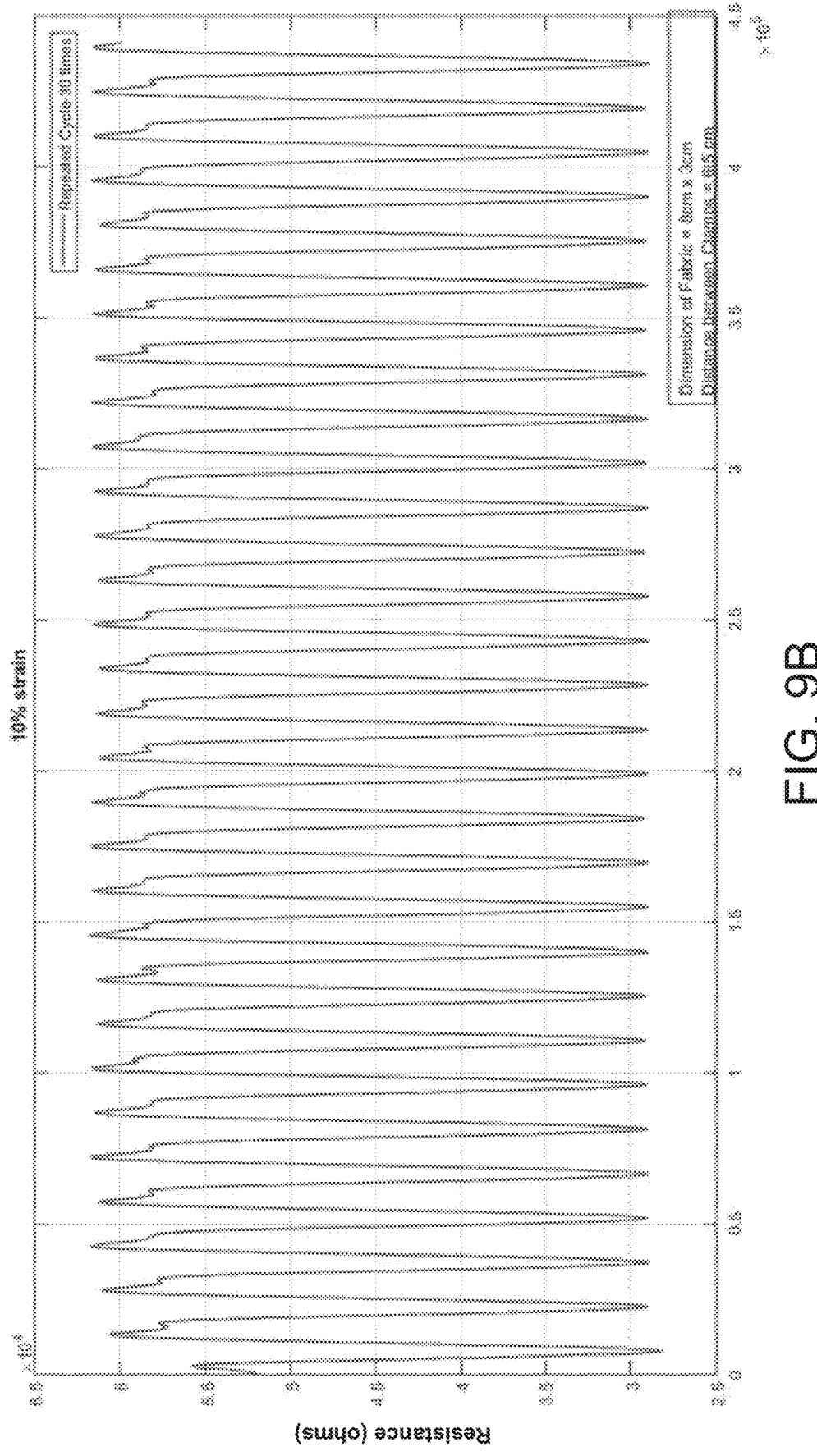

FIGS. 9A-9B are plots showing measured resistance change over time of conductive, piezoresistive elements undergoing length changes (i.e., stretching cycles, repeated 30 times for the same sample), in accordance with some embodiments. The conductive elements were constructed from a conductive elastic fabric having the following properties:

Linear regime of operation: 4 mm or larger

Low hysteresis and low standard deviation, e.g.:

Forward slope: −9890 Ω/mm; standard deviation 221 $\Omega^2$/mm (2.2%)

Backward slope: −8819 Ω/mm; standard deviation 97 $\Omega^2$/mm (1.1%)

The dimensions of the conductive elements used in FIGS. 9A-9B were 8 cm×3 cm, and the distance between the clamps affixed to the conductive elements was 6.5 cm. The plots in FIGS. 9A-9E show that, during operation, once the resistance change of the conductive elements is measured, the electrical circuit (e.g., processor) can detect or calculate the length change corresponding to the measured resistance change. In other words, data from the plots shown in FIGS. 9A-9B can be used as part of a lookup table for the processor to determine the dimension change of the piezoresistive elements.

Figure 10A:
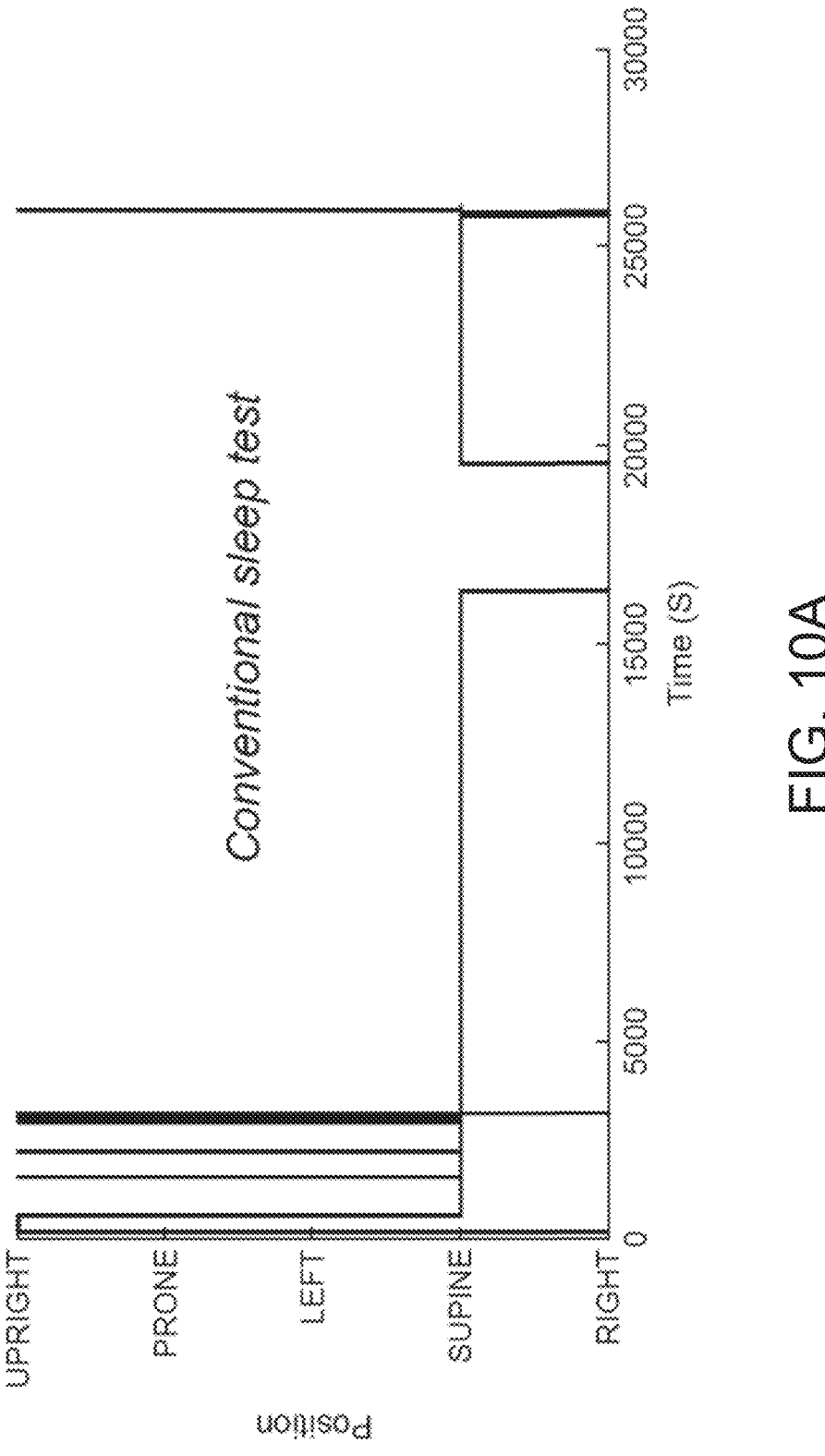
FIGS. 10A and 10B show sleep positions determined by conventional methods and by a method described herein, respectively, in accordance with some embodiments.
Figure 10B:
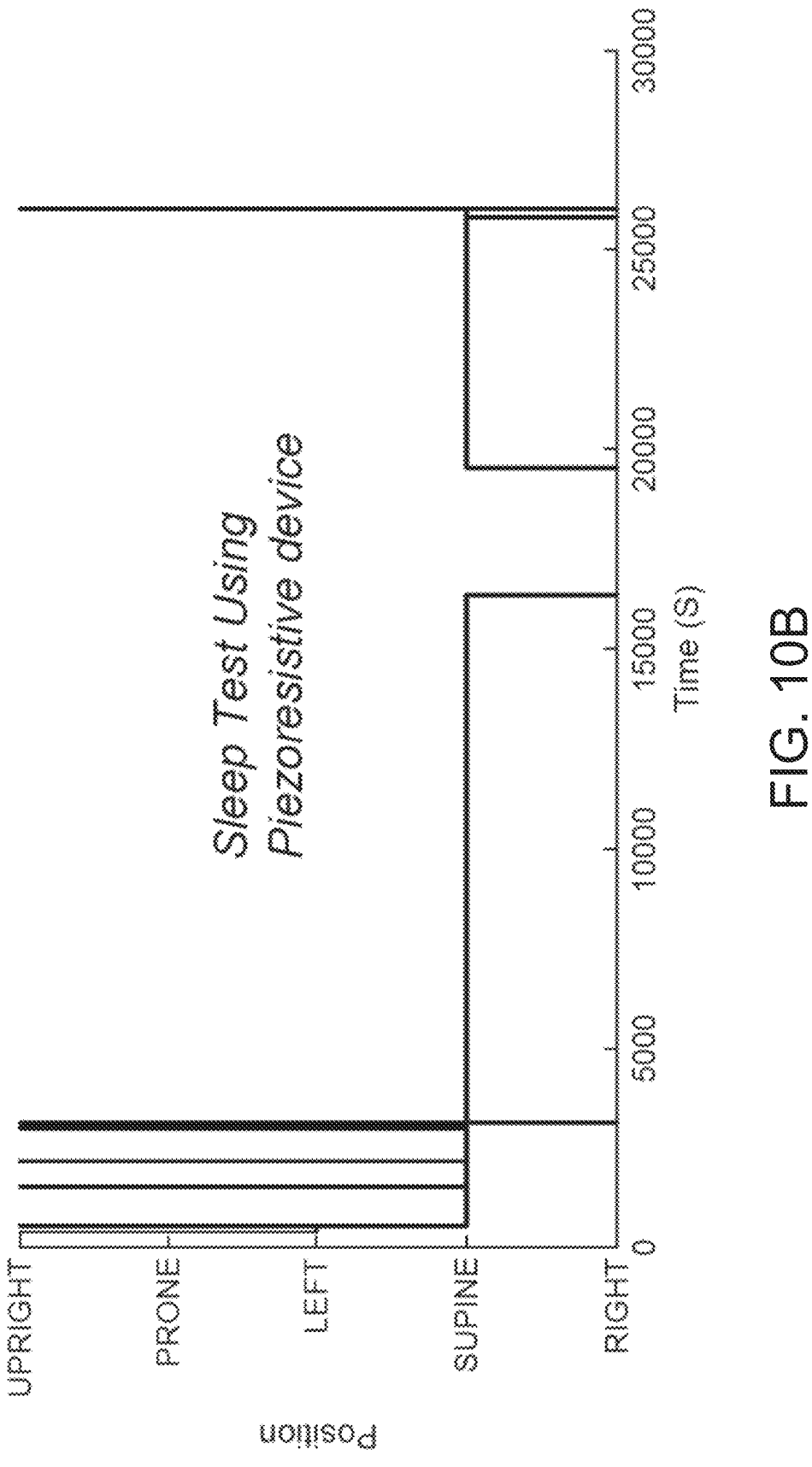

FIGS. 10A and 10B show sleep positions determined by conventional method by a method described herein (including an accelerometer and associated algorithm), respectively, in accordance with some embodiments. In FIGS. 10A and 10B, the sleep positions were divided into five categories: upright, prone, left, supine, and right. The characterizations were conducted over an extended time window of about 8 hours. The conventional method used in FIG. 10A was the home sleep test. The results in FIGS. 10A and 10B agree in 98.5% of the samples. The subject individual being tested slept most of the night on his back (supine), with some periods on the left and right positions.

In operation, monitoring sleep positions can reveal the sleep quality of the user. For example, frequent switching of sleep positions (e.g., between supine and upright) may indicate that the sleep quality of the user is low (e.g., due to insomnia). In addition, the recording of the sleep positions over time can also be analyzed in combination with the respiratory data to determine, for example, which sleep position can lead to the highest sleep quality for the user.

Figure 11A:
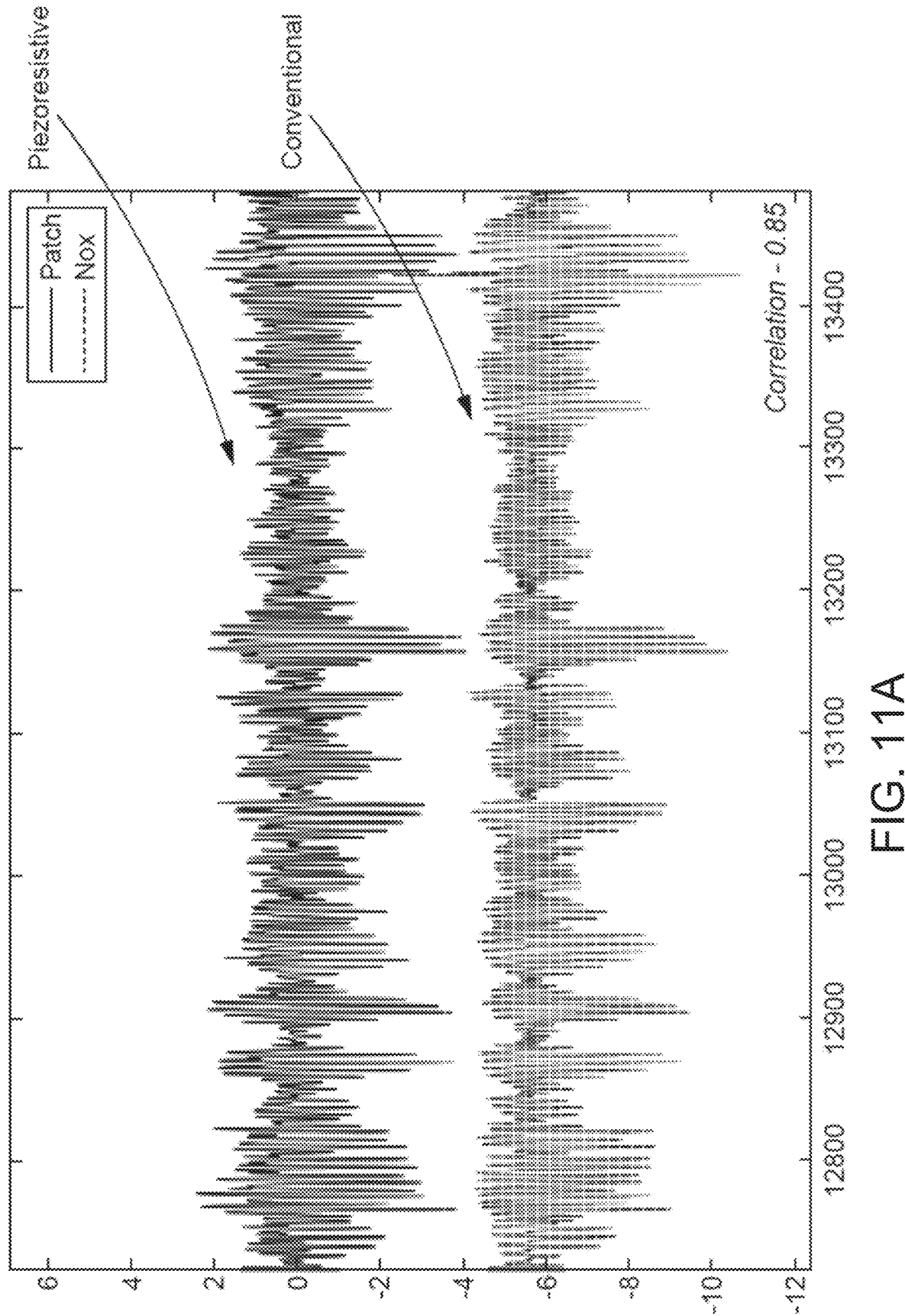
FIGS. 11A and 11B show respiratory efforts measured by conventional methods and by a method described herein within a 10 minute window and within a 1 minute window, respectively, in accordance with some embodiments.
Figure 11B:
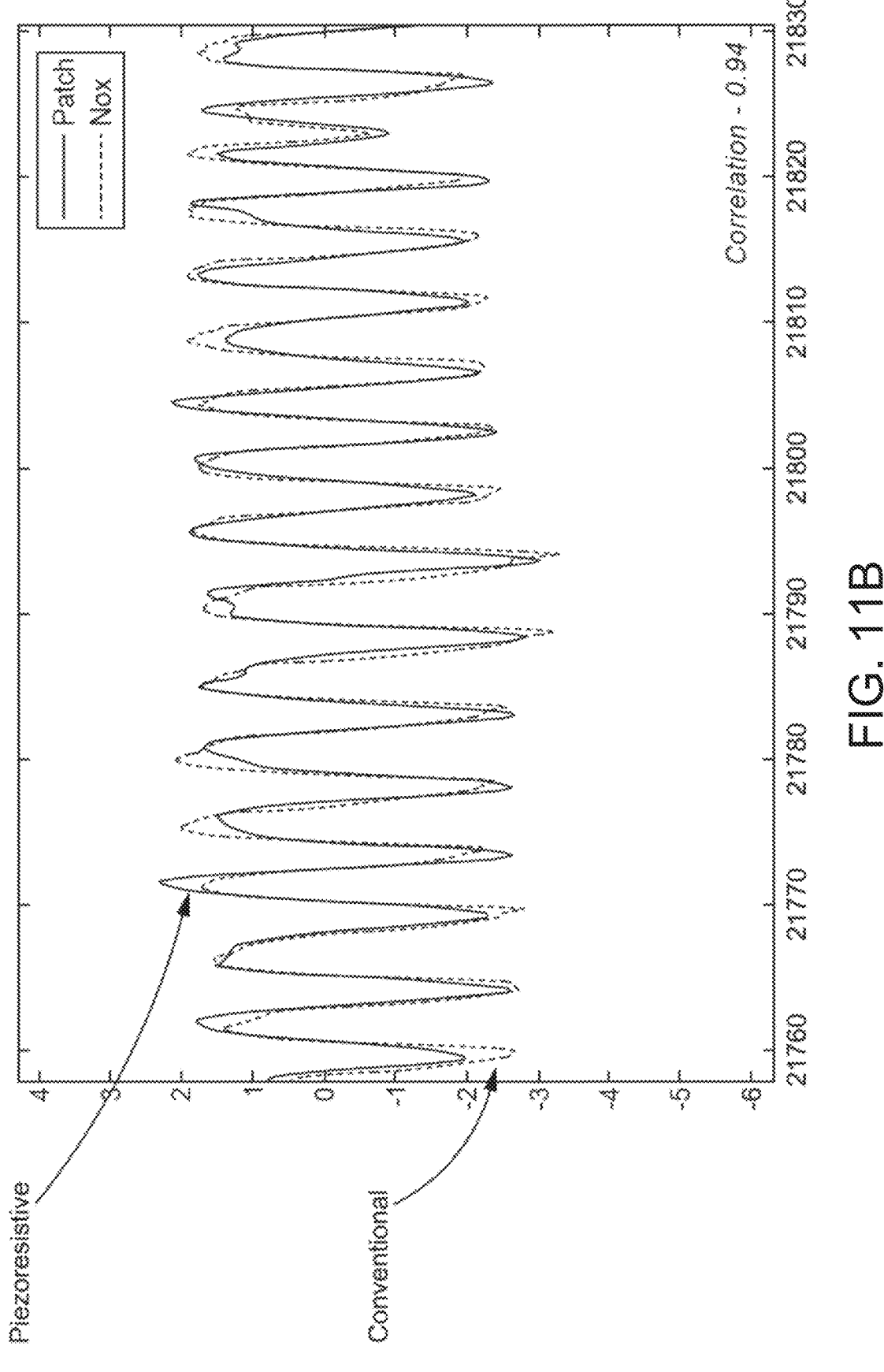

FIGS. 11A and 11B show respiratory efforts measured by conventional methods and by the piezoresistive method described herein, within a 10 minute window and within a 1 minute window, respectively, in accordance with some embodiments. Respiratory efforts were determined based on the measured voltage changes. The piezoresistive method was conducted by attaching the piezoresistive element to the chest of the user (i.e., thorax), and the conventional method was conducted using a Nox T3 portable sleep monitor from Nox Medical. The plots generated by these two methods agree very well with each other. However, the apparatus used in the piezoresistive method is much more compact and affordable while maintaining the high accuracy and reliability of the measurements.

Figure 12:
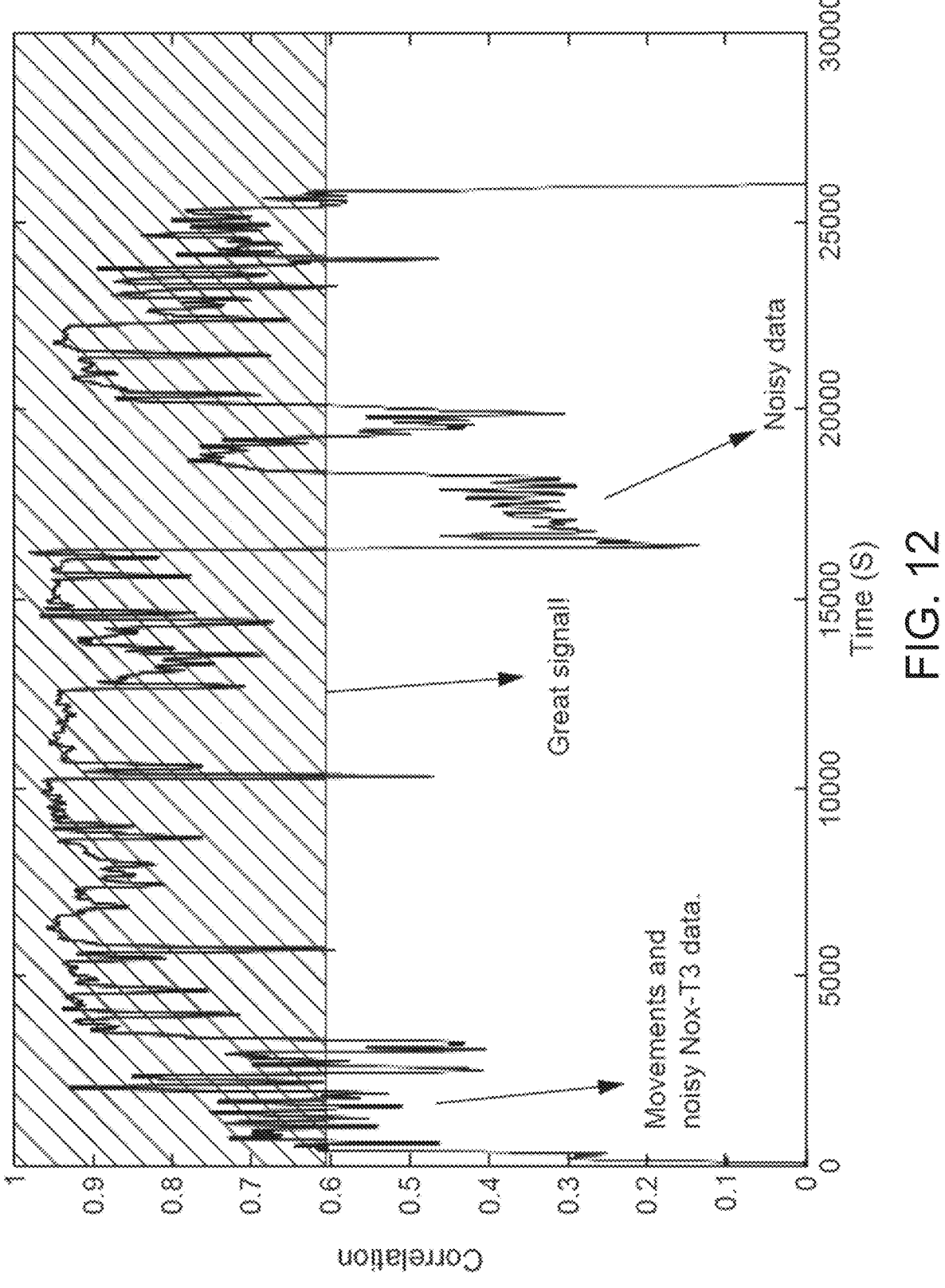
FIG. 12 shows calculated correlation between respiratory data acquired via a piezoresistive method and data acquired via a conventional chest belt in accordance with some embodiments.

FIG. 12 shows calculated correlation between respiratory data acquired via piezoresistive method and data acquired via a conventional chest belt in accordance with some embodiments. The data is acquired over a full night. Great similarity and high-quality signal is obtained over a correlation of about 0.6 (illustrated on graph). The plot in FIG. 12 shows a region of noise signals (labelled on graph), which can be attributed to the sleep posture of the user. In this noisy region, the user slept on his right hand side. Post-processing and design modifications may be employed to reduce the noise and/or increase the signal-to-noise ratio (SNR) of the signals. Therefore, in operation, these noises can be addressed and do not affect the overall performance of the devices.

Figures 13A, 13B:
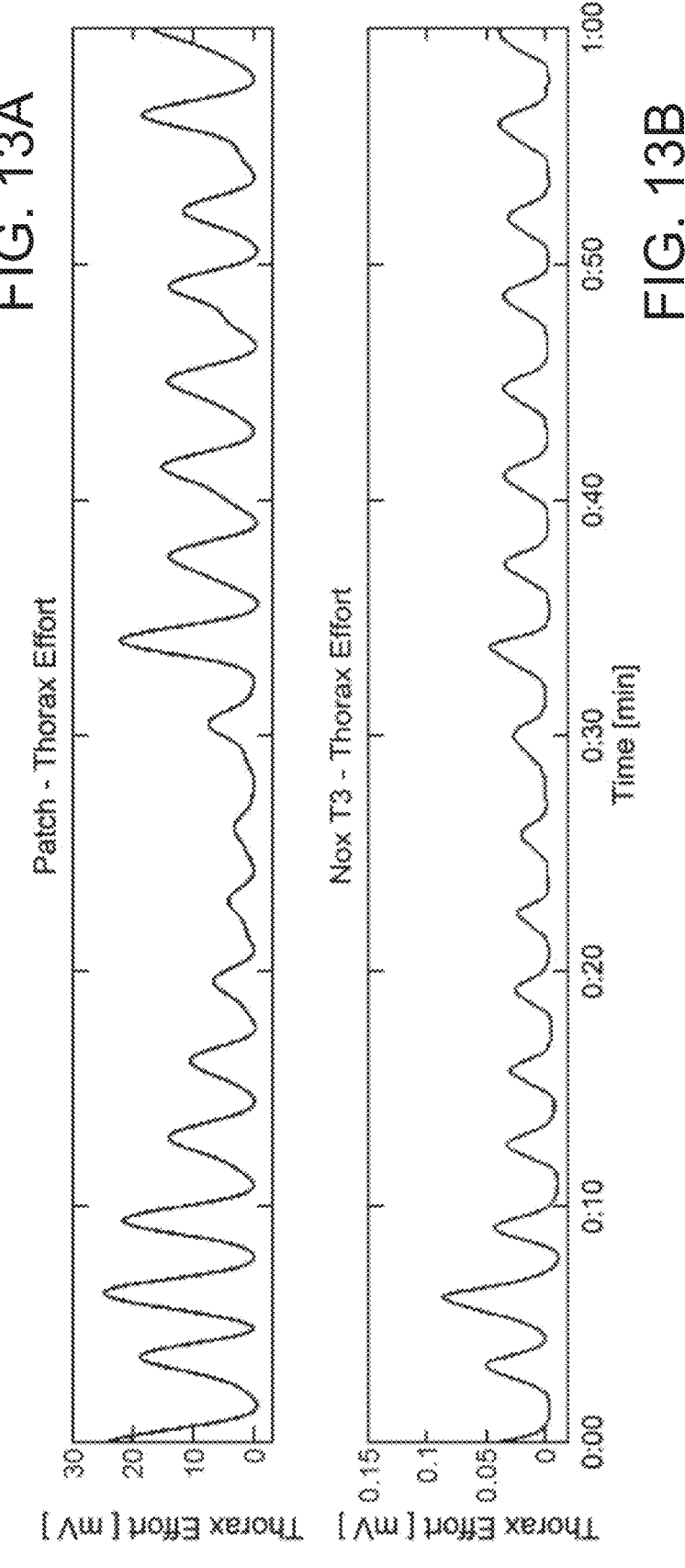
FIGS. 13A and 13B show thorax efforts measured by a conventional method and a method described herein, respectively, over a time span of about 1 minute in accordance with some embodiments.

FIGS. 13A and 13B show thorax efforts measured by conventional method and piezoresistive method, respectively, over a time span of about 1 minute in accordance with some embodiments. The conventional method was performed using a respiratory inductance plethysmography (RIP) belt connected to a NOX T3 sleep monitor. The piezoresistive method is conducted using a patch having a dimension of about 2 inches×3 inches and including a piezoresistive element. The piezoresistive method obtains a clear signal for the respiratory effort measurement, presenting high Pearson's correlation coefficient ($\rho_x$=cov(x,y)/$\sigma_x\sigma_y$) greater than 0.85 over the testing time span of about 60 seconds. In fact the SNR of the signal obtained by the piezoresistive method shown in FIG. 10A is even higher than the SNR of the signal obtained by the conventional method shown in FIG. 10B.

Figure 14:
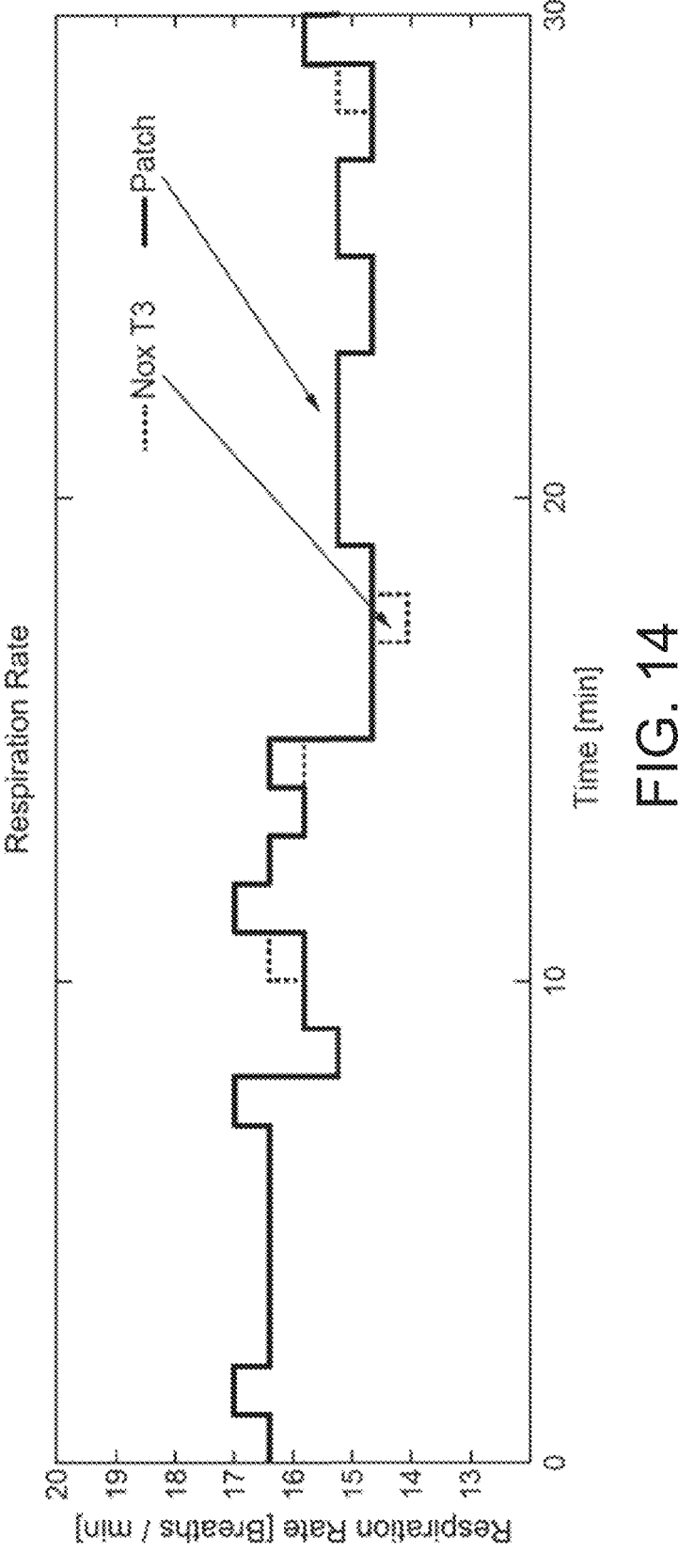
FIG. 14 shows respiration rates measured by conventional methods and by methods described herein, in accordance with some embodiments.

FIG. 14 shows respiration rates measured by conventional methods and the piezoresistive method in accordance with some embodiments. The two plots overlap with each other in most of the regions, demonstrating a high correlation between the two signals. Therefore, the piezoresistive method can be employed to provide a reliable measurement of respiration rates at a much lower cost.

Figures 15A, 15B:
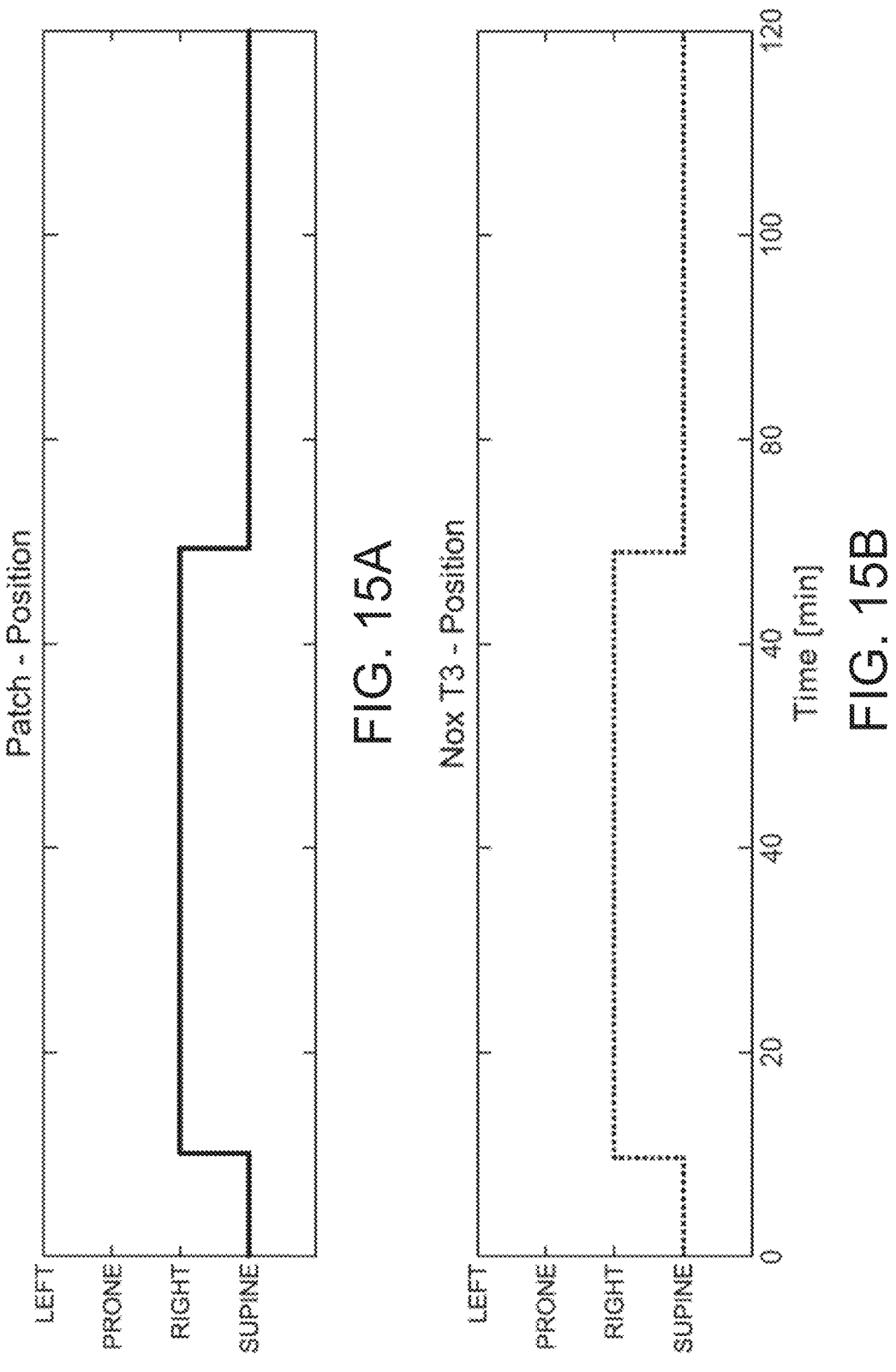
FIGS. 15A and 15B show sleep positions measured by conventional methods and by methods described herein, respectively, in accordance with some embodiments.

FIGS. 15A and 15B show sleep positions measured by conventional methods and the piezoresistive method, respectively, in accordance with some embodiments. Over a time span of about 120 minutes, the sleep positions measured by the two methods are almost identical to each other.

Figures 16A, 16B, 16C:
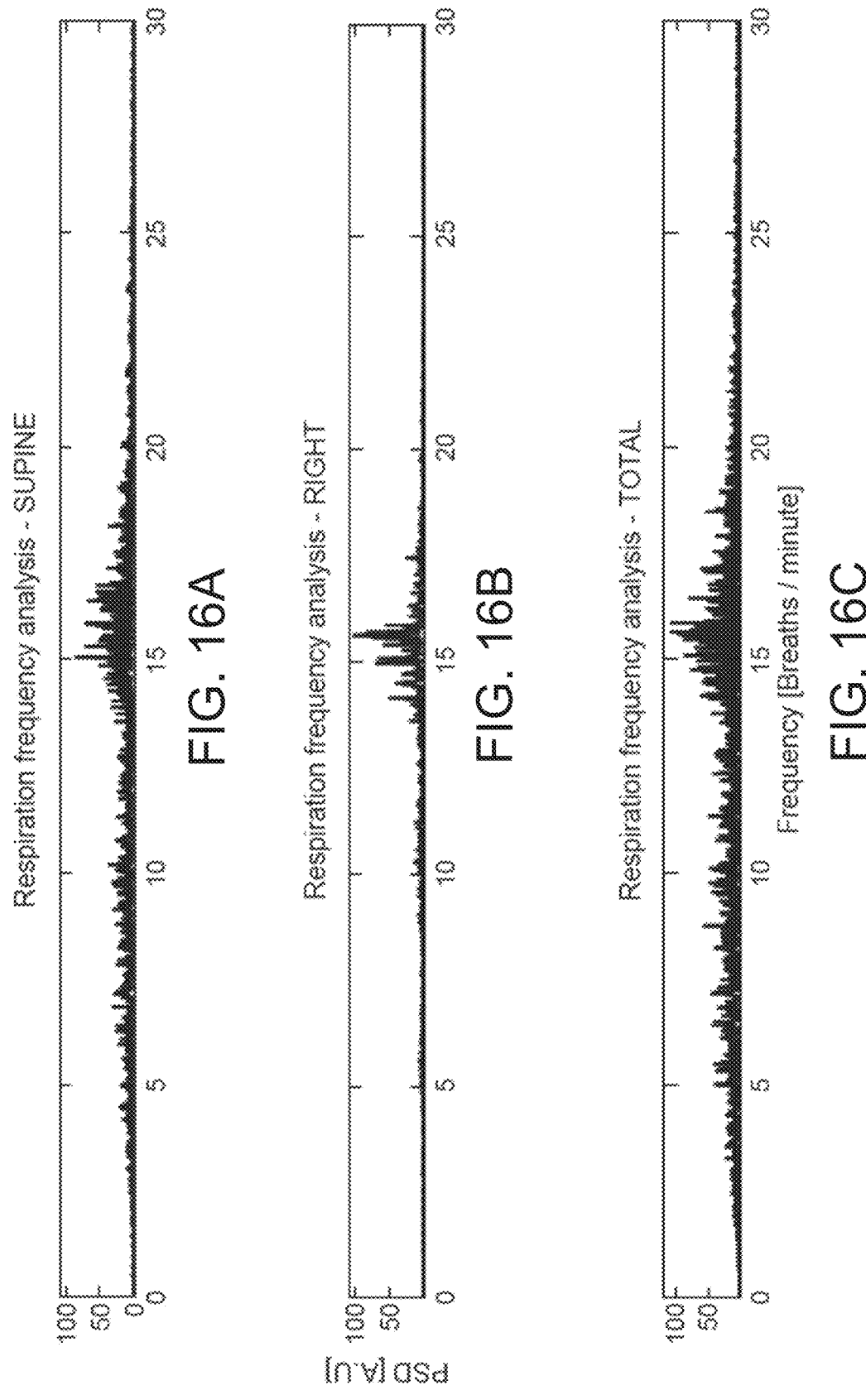
FIGS. 16A-16C show spectral analysis of measured breathing frequency using methods described herein, in accordance with some embodiments.

FIGS. 16A-16C show spectral analysis of measured breathing frequency using the piezoresistive method described herein in accordance with some embodiments. FIG. 16A shows the spectral analysis for the supine position, FIG. 16B shows the spectral analysis for the right position, and the FIG. 16C shows the total spectrum with respect to the breathing frequency without distinguishing different sleep positions. The spectra shown in FIGS. 16A-16C indicate that the user may have different breathing frequencies in different sleep positions. Therefore, this data can be used to optimize the sleep quality of the user by suggesting the user using a particular sleep position.

Figure 17:
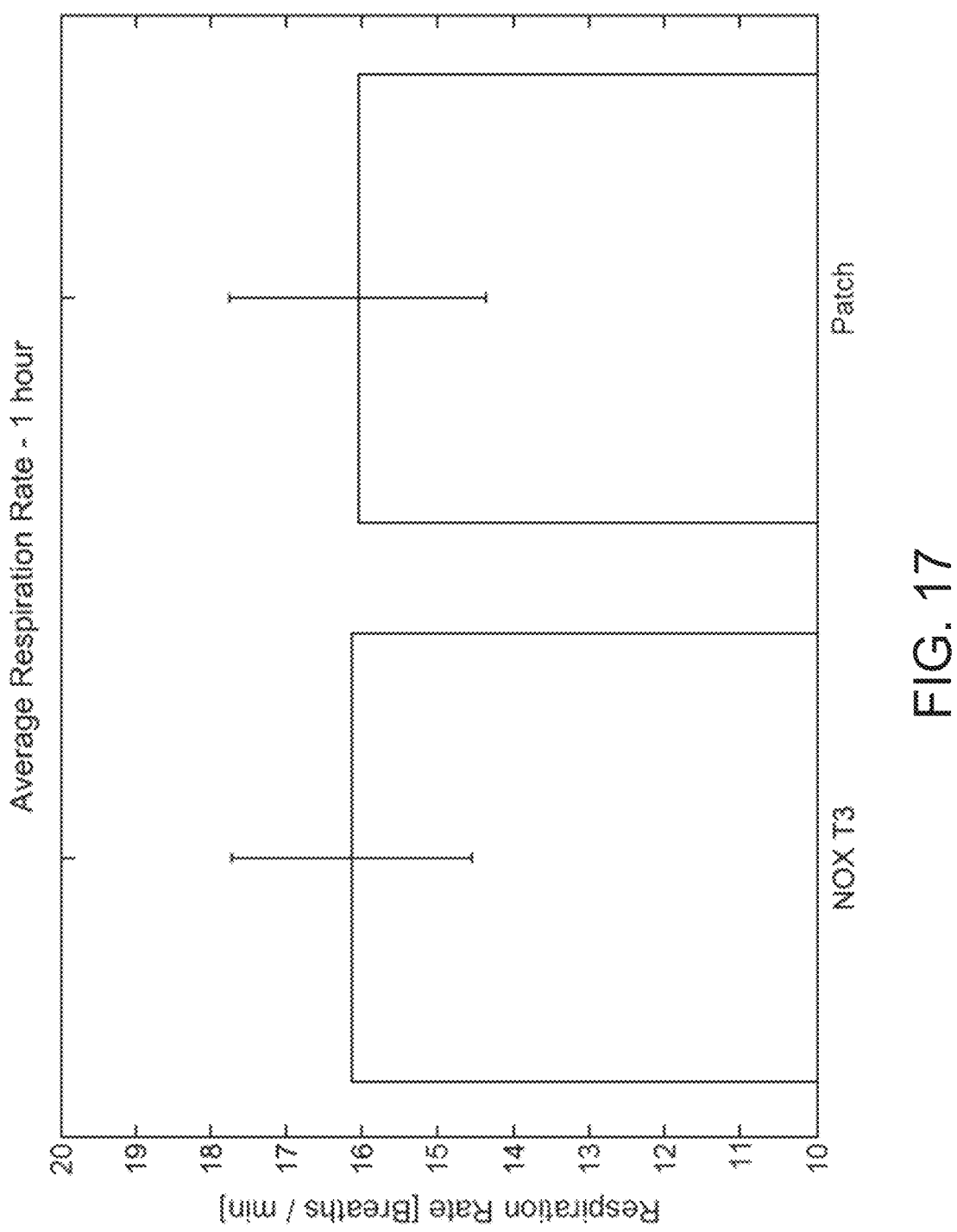
FIG. 17 shows the mean value and standard deviation of respiration rates measured by conventional methods and by methods described herein, in accordance with some embodiments.
Figure 18:
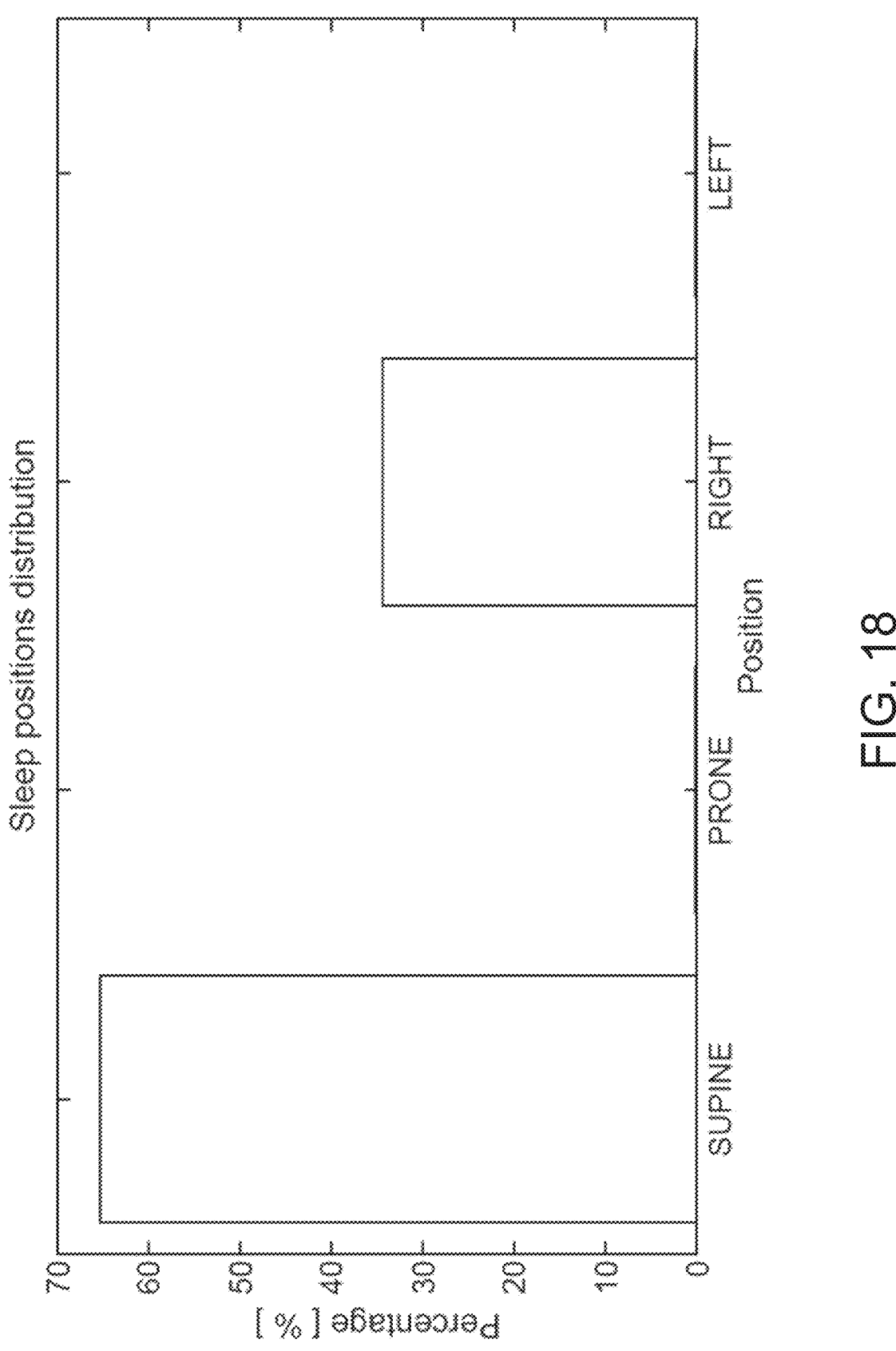
FIG. 18 shows the sleep positions distribution measured by a method described herein, in accordance with some embodiments.

FIG. 17 shows the mean value and standard deviation of respiration rates measured by conventional methods and the piezoresistive method described herein in accordance with some embodiments. FIG. 18 shows the sleep positions distribution measured by the accelerometer method described herein in accordance with some embodiments. These results show high correlation between the measurements from the RIP belt and the piezoresistive device. While the RIP belt is an established method of respiratory effort measurements, the piezoresistive method is more comfortable and compact. The piezoresistive method also allows a constant location of measurement during the night and provides excellent sensitivity without the wires.

Figure 19:
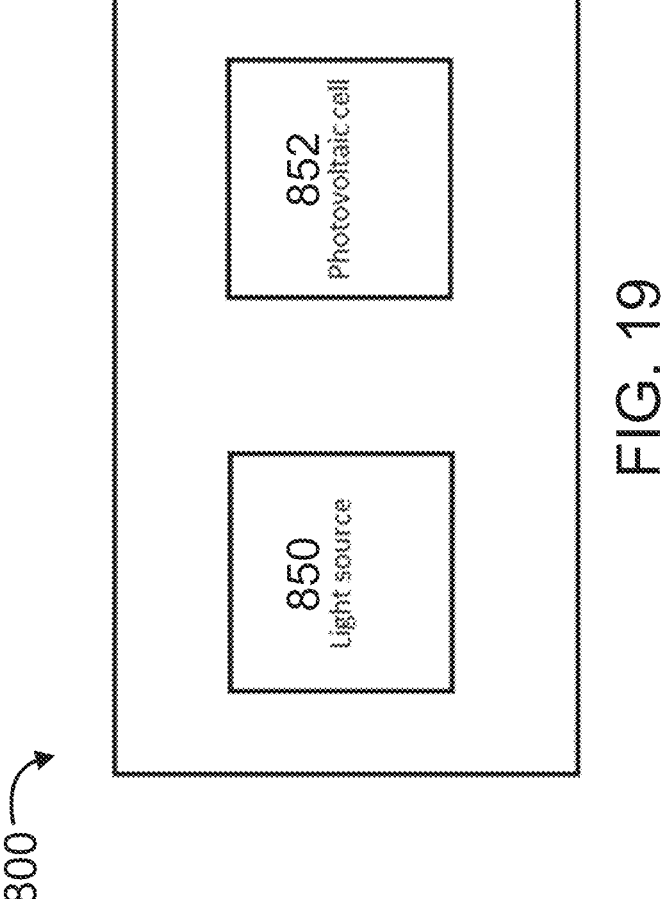
FIG. 19 shows an optical sensor assembly, compatible with apparatuses described herein, in accordance with some embodiments.
Figure 20:
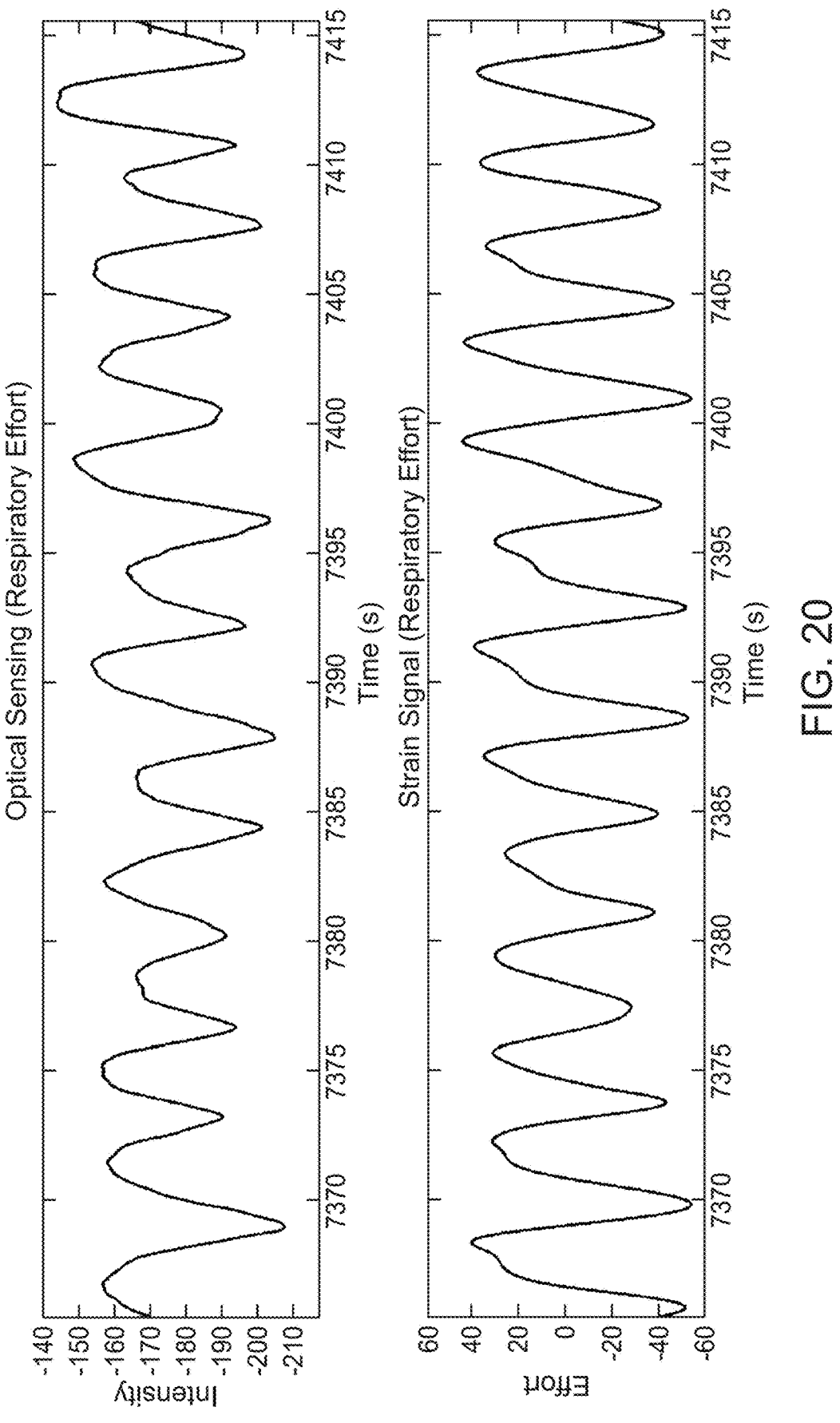
FIG. 20 shows plots of respiratory effort measurements using an optical sensor (upper plot) and using a strain-based method (lower), over time, in accordance with some embodiments.

FIG. 19 shows an optical sensor (photosensor) assembly, compatible with apparatuses described herein, in accordance with some embodiments. As shown in FIG. 19, the photosensor assembly 800 includes one or more light sources (collectively, light source 850) and a photovoltaic cell (or other photodetector) 852. In some embodiments, the light source 850 is configured to emit red or infrared light. Alternatively or in addition, the light source 850 can be configured to emit light at any other wavelength. The light source 850 can be controllable by a controller and/or other electronics onboard, or in wired or wireless communication with the onboard electronics. The photosensor assembly 800 can be incorporated into a patch/apparatus of the present disclosure, and the apparatus can be applied (e.g., adhered) to a surface of a wearer for use. During use, at least a portion of the light emitted from the light source 850 reflects off the skin of the wearer and is detected by the photovoltaic cell (or other photodetector) 852. FIG. 20 compares plots of: (A) respiratory effort measurements taken using an optical sensor such as that described with reference to FIG. 19 (upper plot), and (B) using a strain-based method (lower), over time, in accordance with some embodiments. As shown in FIG. 20, the optical sensor approach captures the respiratory efforts of the wearer with at least as much accuracy as is realized by the strain-based method.

Figure 21:
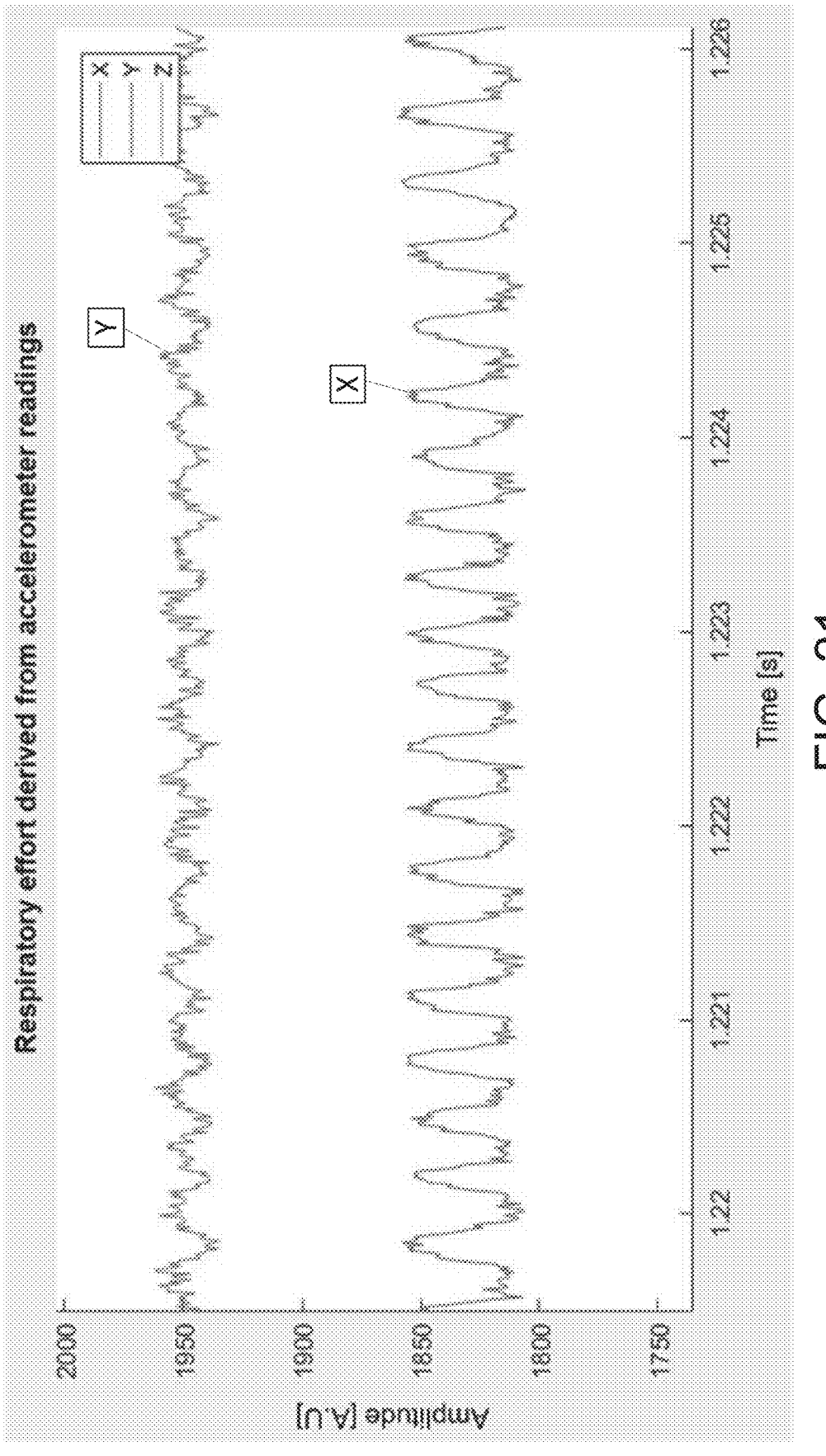
FIG. 21 is a plot showing respiratory effort over time, derived from accelerometer readings for a wearer of an apparatus of the present disclosure, according to some embodiments.

FIG. 21 is a plot showing respiratory effort over time, derived from accelerometer readings for a wearer of an apparatus of the present disclosure, according to some embodiments. As shown in curves X and Y of FIG. 21, the respiratory effort has a periodic variation in amplitude over time, between about 1810 arbitrary units (A.U.) and about 1860 A.U. (for curve X), and between about 1930 A.U. and about 1970 A.U. (for curve Y). The accelerometer for measuring respiratory effort over time can be incorporated into any sensor assembly of the present disclosure.

In some embodiments, an apparatus for measuring respiratory effort of a user includes an adhesive pad, an optical sensor assembly, a power source, and an electrical circuit. The adhesive pad is configured to conform to a surface of the user. The optical sensor assembly is coupled to the adhesive pad, and includes a light source and a photovoltaic cell. The power source is electrically coupled to the optical sensor assembly. The electrical circuit is electrically coupled to the power source and the optical sensor assembly. The electrical circuit can be configured to cause, during use, emission of light from the light source toward a surface of the user, either in a continuous manner or according to a predetermined pattern (ON/OFF toggles). The photovoltaic cell can be configured to detect, during use, reflected light from the surface of the user, such reflected light generated as a consequence of the light emitted from the light source toward the surface of the user.

In some embodiments, determining the respiratory effort of the user according to any apparatus described herein is further based on data collected from an accelerometer of the apparatus.

In some embodiments, an apparatus for measuring respiratory effort of a user includes an adhesive pad, an optical sensor assembly, a power source, and an electrical circuit. The adhesive pad is configured to conform to a surface of the user. The optical sensor assembly is coupled to the adhesive pad, the optical sensor assembly including a light source and a photovoltaic cell. The power source electrically is coupled to the optical sensor assembly. The electrical circuit is electrically coupled to the power source and the optical sensor assembly, and is configured to cause, during use, emission of light from the light source toward a surface of the user. The photovoltaic cell is configured to detect, during use, reflected light from the surface of the user.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, while the embodiments herein describe electrochemical devices such as, for example, lithium ion batteries, the systems, methods, and principles described herein are applicable to all devices containing electrochemically active media. Any electrodes and/or devices including at least an active material (source or sink of charge carriers), an electrically conducting additive, and an ionically conducting media (electrolyte) such as, for example, batteries, capacitors, electric double-layer capacitors (e.g., ultracapacitors), pseudo-capacitors, etc., are within the scope of this disclosure. Furthermore, embodiments may be used with non-aqueous and/or aqueous electrolyte battery chemistries.

In another example, embodiments may be implemented using hardware, software or a combination thereof. When implemented in software, the software code can be executed on any suitable processor or collection of processors, whether provided in a single computer or distributed among multiple computers. Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the retention/delivery structure disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus for monitoring a sleep parameter of a user, the apparatus comprising:
   a pad configured to conform to a surface of the user;
   a first stretchable element coupled to the pad, the first stretchable element configured to exhibit a modified electrical property in response to an applied force;
   a second stretchable element coupled to the pad and extending from the first stretchable element;
   a third stretchable element coupled to the pad and extending from the second stretchable element;
   a power source electrically coupled to the first stretchable element; and
   an electrical circuit electrically coupled to the power source and the first stretchable element, the electrical circuit configured to detect, during use, a change in an electrical property of the first stretchable element.

2. The apparatus of claim 1, wherein the first stretchable element is in a neutral stress state prior to being coupled to the pad, and is in a non-neutral stress state upon being coupled to the pad.

3. The apparatus of claim 1, wherein, during use, the first stretchable element transitions from a tensile state, through a neutral stress state, to a compressed state, in response to an exhalation of the user.

4. The apparatus of claim 1, wherein the first stretchable element includes a substrate coated with a conductive material.

5. The apparatus of claim 1, wherein the first stretchable element includes fibers coated with a conductive polymer.

6. The apparatus of claim 1, wherein the first stretchable element includes a nonwoven fabric.

7. The apparatus of claim 1, wherein the first stretchable element includes polyester, nylon, or glass.

8. The apparatus of claim 1, wherein the first stretchable element includes a semiconductor material.

9. The apparatus of claim 1, wherein the first stretchable element, the second stretchable element, and the third stretchable element have a common composition.

10. The apparatus of claim 1, wherein at least two of the first stretchable element, the second stretchable element, and the third stretchable element differ in composition.

11. An apparatus for monitoring a sleep parameter of a user, the apparatus comprising:

a pad configured to conform to a surface of the user;

a plurality of stretchable elements coupled to the pad, a first stretchable element from the plurality of elements configured to exhibit a modified electrical property in response to an applied force, and a second stretchable element from the plurality of elements not configured to exhibit a modified electrical property in response to an applied force;

a power source electrically coupled to the first stretchable element; and an electrical circuit electrically coupled to the power source and the first stretchable element, the electrical circuit configured to detect, during use, a change in an electrical property of the first stretchable element.

12. The apparatus of claim 11, wherein the first stretchable element is in a neutral stress state prior to being coupled to the pad, and is in a non-neutral stress state upon being coupled to the pad.

13. The apparatus of claim 11, wherein, during use, the first stretchable element transitions from a tensile state, through a neutral stress state, to a compressed state, in response to an exhalation of the user.

14. The apparatus of claim 11, wherein the first stretchable element includes a substrate coated with a conductive material.

15. The apparatus of claim 11, wherein the first stretchable element includes fibers coated with a conductive polymer.

16. The apparatus of claim 11, wherein the first stretchable element includes a nonwoven fabric.

17. The apparatus of claim 11, wherein the first stretchable element includes polyester, nylon, or glass.

18. The apparatus of claim 11, wherein the first stretchable element includes a semiconductor material.

19. The apparatus of claim 1, wherein the first stretchable element, the second stretchable element, and the third stretchable element have a common composition.

20. The apparatus of claim 1, wherein at least two of the first stretchable element, the second stretchable element, and the third stretchable element differ in composition.

\* \* \* \* \*